(12) United States Patent
Tetsu et al.

(10) Patent No.: US 7,358,086 B2
(45) Date of Patent: Apr. 15, 2008

(54) MAMMALIAN TWO-HYBRID SYSTEM FOR SCREENING FOR MODULATORS OF THE ACCUMULATION OF METABOLIC PRODUCTS

(75) Inventors: Osamu Tetsu, San Francisco, CA (US); Kenichi Wakita, San Francisco, CA (US); Frank McCormick, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 70 days.

(21) Appl. No.: 10/896,600

(22) Filed: Jul. 21, 2004

(65) Prior Publication Data

US 2004/0265791 A1 Dec. 30, 2004

Related U.S. Application Data

(63) Continuation-in-part of application No. 09/687,593, filed on Oct. 13, 2000, now Pat. No. 6,787,321.

(51) Int. Cl.
C12N 5/22 (2006.01)

(52) U.S. Cl. .................. 435/367; 435/371; 435/372; 435/320.1; 536/23.4

(58) Field of Classification Search ................ 435/325, 435/7.2
See application file for complete search history.

(56) References Cited

U.S. PATENT DOCUMENTS

| | | | |
|---|---|---|---|
| 5,468,614 | A | 11/1995 | Fields et al. |
| 5,525,490 | A | 6/1996 | Erickson et al. |
| 5,851,775 | A | 12/1998 | Barker et al. |
| 5,885,779 | A | 3/1999 | Sadowski et al. |
| 5,905,025 | A | 5/1999 | Marsolier et al. |
| 5,948,620 | A | 9/1999 | Hurd et al. |
| 5,955,280 | A | 9/1999 | Vidal et al. |
| 5,965,368 | A | 10/1999 | Vidal et al. |
| 6,051,381 | A | 4/2000 | Kornacker |
| H1892 | H | 10/2000 | Klein et al. |
| 6,242,253 | B1 | 6/2001 | Karin et al. |

FOREIGN PATENT DOCUMENTS

| | | |
|---|---|---|
| EP | 0 370 813 A2 | 5/1990 |
| WO | WO 98/05754 A | 2/1998 |

OTHER PUBLICATIONS

Tirode et al., J. Biol. Chem., vol. 272, No. 37 (1997), pp. 22995-22999.*

Finley et al., (1997) in The Yeast Two-Hybrid System, eds. P. Bartel, S. Fields, Oxford University Press, pp. 197-214.

Nagahara et al., (1998) Nature Medicine, vol. 4, 1449-1452.

Schwarze et al., (1999) Science, vol. 285, 1569-1572.

Young (1998), Biology of Reproduction, vol. 58 pp. 302-311.

Hwang, Jung-Joo et al. "Novel retroviral vector transferring a suicide gene and a selectable marker gene with enhanced gene expression by using a tetracycline-responsive expression system." Journal of Virology, vol. 70, No. 11, 1996, pp. 8138-8141.

Kametaka, Minako et al. Introduction of an inducible suicide system into CTLL-2 using Fas-estrogen receptor chimera for cytotoxicity modulation. Blood, vol. 96, No. 11, part 2, 2000, pp. 311b.

Aberle et al. (1997) "∃-catenin is a target for the ubiquitin-proteasome pathway," EMBO J. 16:3797-3804.

Dang et al. (1991) "Intracellular Leucine Zipper Interactions Suggest c-Myc Hetero-Oligomerization," Mol. Cell. Biol. 11:954-962.

Fearon et al. (1992) "Karyoplasmic interaction selection strategy: A general strategy to detect protein-protein interactions in mammalian cells." Proc. Natl. Acad. Sci. USA 89:7957-7962.

(Continued)

*Primary Examiner*—James Ketter
(74) *Attorney, Agent, or Firm*—Quine Intellectual Property Law Group, P.C.; Gary Baker

(57) ABSTRACT

This invention utilizes a two-hybrid system to screen for agents that modulate the ability of a cell to degrade or to accumulate a metabolic product or to selective kill a cell or to selectively express a gene or cDNA in a cell that has a defect in its ability to degrade or to accumulate a metabolic product. One embodiment provides a mammalian cell comprising a nucleic acid encoding a peptide binding domain and an effector gene; a first chimeric protein comprising a nucleic acid binding domain that binds the peptide binding domain attached to the metabolic product or to a ligand that binds to the metabolic product; and a second chimeric protein comprising an expression control protein attached to the metabolic product or to the ligand that binds to the metabolic product such that when the first chimeric protein comprises the metabolic product, the second chimeric protein comprises the ligand and when the first chimeric protein comprises the ligand, the second chimeric protein comprises the metabolic product. The cell is contacted with a test agent and an alteration of expression of the effector gene is detected (if present) where a change in expression of the effector gene in response to the test agent indicates that the test agent modulates the ability of the cell to accumulate or degrade the metabolic product.

28 Claims, 5 Drawing Sheets

OTHER PUBLICATIONS

Harada (1990) "Intestinal polyposis in mice with a dominant stable mutation of the β-catenin gene," EMBO J. 18:5931-5942.

He et al. (1998) "Identification of a c-MYC as a Target of the APC pathway." Science 281:1509-1512.

He et al. (1999) "PPAR Is an APC-Regulated Target of Nonsteroidal Anti-Inflammatory Drugs." Cell, 99:335-345.

Kinzler and Vogelstein (1996) "Lessons from Hereditary Colorectal Cancer." Cell, 87:159-170.

Kinzler et al. (1991) "Identification of FAP Locus Genes from Chromosome 5q21." Science 253:661-665.

Korinek et al (1997) "Constitutive Transcriptional Activation by a β-catenin-Tcf Complex in APC$^{-/-}$ Colon Carcinoma." Science 275: 1784-1787.

Morin et al. (1997) "Activation of a β-catenin-Tcf Signaling in Colon Cancer by Mutations in β-catenin or APC." Science 275: 1787-1790.

Larent-Puig et al. (1990) "Sequence of Molecular genetic events in colorectal tumorigenesis." Eur. J. Cancer Prev., 8: Suppl 1 S39-47.

Mandl et al. (1998) "In vitro-synthesized infectious RNA as an attenuated live vaccine in a flavivirus model." Nat Med. 4:1438-1440.

Munemitsu et al. (1996)"Regulation of intracellular β-catenin levels by the adenomatous polyposis coli (APC) tumor-suppressor protein." Proc. Natl. Acad. Sci. USA 92:3046-3050.

Munemitsu et al (1996) "Deletion of an Amino Terminal Sequence Stabilizes β-catenin In Vivo and Promotes Hyperphosphorylation of the Adenomatous Polyposis Coli Tumor Suppressor Protein." Mol. Cell. Biol. 16:4088-4094.

Nagahara et al. (1998) "Transduction of full-length TAT fusion proteins into mammalian cells:TAT-p27$^{kip1}$ induces cell migration." Nat Med 4:1449-1452.

Nishisho et al. (1991) "Mutations of Chromosomes 5q21 Genes in FAP and Colorectal Cancer Patients." Science 253:665-669.

Rubinfeld et al (1996) "Binding of GSK3β to the APC-β-Catenin Complex and Regulation of Complex Assembly." Science 272:1023-1026.

Shibata et al. (1997) "Rapid Colorectal Adenoma Formation Initiated by Conditional Targeting of the Apc Gene." Science 278:120-123.

Sparks et al. (1998) "Mutational Analysis of the APC/β-Catenin/Tcf Pathway in Colorectal Cancer." Cancer Res. 58:1130-1134.

Tetsu and McCormick (1999) "β-Catenin regulates expression of cyclin D1 in colon carcinoma cells." Nature 398:422-426.

Vandier et al. (1988) "Selective Killing of Glioma Cell Lines Using an Astrocyte-specific Expression of the Herpes Simplex Virus-Thymidine Kinase Gene." Cancer Res. 58:4577-4580.

Verma and Somia (1997) "Gene Therapy—promises, problems and prospects." Nature 389:239-242.

Winston et al. (1999) The SCF$^{\beta-T\ RC\ P}$-Ubiquitin ligase complex associates specificity with phosphorylated destruction motifs in 16B∀ and β-catenin and stimulated 16B∀ ubiquitination in vitro. Genes Dev. 13-270-283.

Le Douarin et al (1995) "A new version of the two-hybrid assay for detection of protein-protein interactions," Nucleic Acids Research, vol. 23., No. 5.

Montross et al. (2000) "A β-Catenin/engrailed chimera selectively suppresses Wnt signaling," Journal of Cell Research, 113:1759-1770.

Wakita et al. (2000) "A Mammalian Two-hybrid System for Adenomatous Polyposis Coli-Mutated Colon Cancer Therapeutics," Cancer Research 61:854-858.

* cited by examiner

MAMMALIAN TWO-HYBRID SYSTEM FOR SCREENING FOR MODULATORS OF THE ACCUMULATION OF METABOLIC PRODUCTS

CROSS-REFERENCE TO RELATED APPLICATIONS

This application is a divisional application of, and claims priority to and the benefit of, United States Utility patent application Ser. No. 09/687,593, "Mammalian Two-Hybrid System for Screening for Modulators of the Accumulation of Metabolic Products", by Osamu Tetsu, et al., filed Oct. 13, 2000.

FIELD OF THE INVENTION

This invention pertains to the fields of molecular biology and oncology. In particular, this invention provides a novel two-hybrid system two-hybrid system to screen for agents that modulate the ability of a cell to degrade a metabolic product (e.g. certain cancer cells) or to selectively kill a cell that has a defect in its ability to degrade a metabolic product.

BACKGROUND OF THE INVENTION

A wide variety of diseases are characterized by the abnormal accumulation of one or more metabolic products. Such diseases, sometimes referred to as "storage diseases" are typically caused by the increased accumulation of metabolic products (e.g., lipids, proteins, complex carbohydrates, etc.) due to either the inactivity of an enzyme that degrades the products or the hyperactivity of an enzyme that creates the products. Storage disease include but are not limited to glycogen storage disease I, GM1 gangliosidoses, MPS IV B (Morquio B), GM2 gangliosidoses (O, B, AB, B1 variants), Niemann-Pick disease (A, B, and C), Metachromatic leukodystrophy (arylsulfatase A and SAP-1 deficient), Krabbe disease, Fabry disease, Gaucher disease, Farber disease, Wolman disease (cholesterol ester storage disease), MPS I (Hurler and Scheie syndromes), MPS II (Hunter syndrome), MPS III A, C, and D (Sanfilippo A, C, and D), PS III B (Sanfilippo B), MPS IV A (Morquio A), MPS VI (Maroteaux-Lamy syndrome), MPS VII (beta-glucuronidase deficiency), Multiple sulfatase deficiency, Mucolipidosis I (Sialidosis), Mucolipidosis II & III, alpha-Mannosidosis, beta-Mannosidosis, Fucosidosis, Sialic acid storage disease, Galactosialidosis, and Aspartylglucosaminuria Cystinosis.

Historically, storage diseases have been treated by supplementing the "missing" enzymatic activity. Thus, for example, Gaucher's disease can be treated by use of a glucocerebrosidase targeted to spleen cells. Similarly, superoxide dismutase can be targeted to the liver as an antioxidant, and so forth.

Such approaches typically have seen limited success. Often the "therapeutic agent" must be specifically targeted to a particular organ or tissue. In addition consistent delivery of the targeted therapeutic agent at physiologically relevant concentrations has proven difficult. In addition, the identification of viable therapeutic agents has proven difficult.

SUMMARY OF THE INVENTION

This invention provides novel approaches to the treatment (e.g. amelioration of one or more symptoms) of pathological states characterized by the undesired accumulation of one or more metabolic products. In addiction, this invention provides effective systems in which to screen for agents that modulate the ability of a cell to accumulate and/or degrade a metabolic product.

In preferred embodiments, this invention utilizes a two-hybrid system to screen for agents that modulate the ability of a cell to degrade or to accumulate a metabolic product or to selectively kill a cell or to selectively express a gene or cDNA in a cell that has a defect in its ability to degrade or to accumulate a metabolic product. In one such embodiment, this invention provides a method of screening for an agent that modulates the ability of a cell to accumulate or to degrade a metabolic product. The method involves providing a mammalian cell comprising a nucleic acid encoding a peptide binding domain and an effector gene; a first chimeric protein comprising a nucleic acid binding domain that binds the peptide binding domain attached to the metabolic product or to a ligand that binds to the metabolic product; and a second chimeric protein comprising an expression control protein attached to the metabolic product or to the ligand that binds to the metabolic product such that when the first chimeric protein comprises the metabolic product, said second chimeric protein comprises the ligand and when the first chimeric protein comprises the ligand, said second chimeric protein comprises the metabolic product. The cell is contacted with one or more test agent(s) and alteration of alteration of expression of the effector gene is detected wherein a difference in the expression of the effector gene in the test cell, as compared to a control cell contacted with a lower concentration of test agent or no test agent indicates that the test agent(s) modulate the ability of said cell to accumulate or degrade the metabolic product.

In particularly preferred embodiments, the expression control protein is a transactivator (e.g. VP16) or a repressor. Particularly preferred nucleic acid binding proteins include, but are not limited to GAL-4, and GAL-4-Y. In certain embodiments, preferred effectors include, but are not limited to, a reporter gene (e.g., chloramphenicol acetyl transferase (CAT), luciferase, b-galactosidase (b-gal), alkaline phosphatase, horse radish peroxidase (HRP), growth hormone (GH), green fluorescent protein (GFP), etc.), a cytotoxin (e.g., thymidine kinase, pseudomonas exotoxin, diphtheria toxin, ricin, abrin, etc.), and/or an apoptosis inducing (e.g., P53, P73, Bax, Bad, FADD, a caspase gene, etc.). In various embodiments, the ligand and metabolic product respectively include, but are not limited to a beta-catenin and a Tcf, a NF-kB and I-kB, a P53 and MDM2, a receptor and its heteromelic receptor partner.

The first and/or the second chimeric protein(s) are expressed from a nucleic acid in the cell (e.g. under control of an inducible (e.g. ecdysone promoter), tissue-specific, or constitutive promoter), or the first and/or the second chimeric protein is a protein transported into the cell, e.g. by using a protein comprising an HIV TAT domain.

Preferred cells for the practice of the methods of this invention include, but are not limited to SW480, SW48, DLD-1, HCT-116, HT29, 293, U-20S, T-47D, MCF-7, HeLa, A549, Hep G2, and/or Jarkat cell.

In one particularly preferred embodiment the nucleic acid encodes a GAL-4 binding site, the effector gene is a reporter gene, the first chimeric protein comprises a GAL-4 nucleic acid binding protein and a beta catenin or a Tcf; and the second chimeric protein comprises a VP-16 and beta catenin or a Tcf. One particularly preferred Tcf is Tcf4.

In certain embodiments, the cell further comprises a second nucleic acid encoding the ligand or metabolic product operably linked to an inducible promoter (e.g. an ecdysone promoter).

In another embodiment, this invention provides a method of selectively expressing an effector gene in a cell that accumulates or degrades a metabolic product. The method involves providing a cell comprising a nucleic acid encoding a peptide binding site and an effector gene, a first chimeric protein comprising a nucleic acid binding protein that binds the peptide binding domain where the nucleic acid binding protein is attached to the metabolic product or to a ligand that binds to said metabolic product, and a second chimeric protein comprising an expression control protein attached to the metabolic product or to a ligand that binds to the metabolic product such that when said first chimeric protein comprises the metabolic product, said second chimeric protein comprises the ligand and when the first chimeric protein comprises the ligand, said second chimeric protein comprises the metabolic product; whereby the cell, in the absence of the ability to degrade the metabolic product or the ligand that binds the metabolic product activates or represses expression of said effector gene. A preferred expression control protein is a transactivator (e.g. VP16) or a repressor. Preferred nucleic acid binding proteins, effector genes, ligands and metabolic products include, but are not limited to those described above.

The first and/or the second chimeric protein(s) are expressed from a nucleic acid in the cell (e.g. under control of an inducible (e.g. ecdysone promoter), tissue-specific, or constitutive promoter), or the first and/or the second chimeric protein is a protein transported into the cell, e.g. by using a protein comprising an HIV TAT domain.

Preferred cells for the practice of the methods of this invention include, but are not limited to SW480, SW48, DLD-1, HCT-116, HT29, 293, U-20S, T-47D, MCF-7, HeLa, A549, Hep G2, and/or Jarkat cell.

In one particularly preferred embodiment the nucleic acid encodes a GAL-4 binding site, the effector gene is a reporter gene, the first chimeric protein comprises a GAL-4 nucleic acid binding protein and a beta catenin or a Tcf; and the second chimeric protein comprises a VP-16 and beta catenin or a Tcf. One particularly preferred Tcf is Tcf4.

This invention also provides methods of selectively killing a cell that accumulates a metabolic product (e.g. certain cancer cells). The methods involve transfecting the cell with a nucleic acid encoding a peptide binding site and an effector that is a cytotoxin or an apoptosis-inducing gene; introducing into the cell a first chimeric protein comprising a nucleic acid binding protein that binds the peptide binding domain where said nucleic acid binding protein is attached to said metabolic product or to a ligand that binds to said metabolic product; and introducing into the cell a second chimeric protein comprising a transactivator (e.g. VP16) attached to said metabolic product or to said ligand that binds to said metabolic product, such that when said first chimeric protein comprises said metabolic product, said second chimeric protein comprises said ligand and when said first chimeric protein comprises said ligand, said second chimeric protein comprises said metabolic product. Preferred nucleic acid binding proteins include, but are not limited to, GAL-4 and GAL-4-Y. In one preferred embodiment, the effector is a cytotoxin (e.g. thymidine kinase, pseudomonas exotoxin, diphtheria toxin, ricin, abrin, etc.). In certain preferred embodiments, the effector is an apoptosis-inducing gene (e.g. P53, P73, Bax, Bad, FADD, a caspase (e.g. Casp3, Casp9, Apaf1, etc.), etc.). In various embodiments, the ligand and metabolic product respectively include, but are not limited to a beta-catenin and a Tcf, a NF-kB and I-kB, a P53 and MDM2, a receptor and its heteromelic receptor partner.

The first and/or the second chimeric protein(s) are expressed from a nucleic acid in the cell (e.g. under control of an inducible (e.g. ecdysone promoter), tissue-specific, or constitutive promoter), or the first and/or the second chimeric protein is a protein transported into the cell, e.g. by using a protein comprising an HIV TAT domain. Suitable cells include, but are not limited to SW480, SW48, DLD-1, HCT-116, HT29, 293, U-20S, T-47D, MCF-7, HeLa, A549, Hep G2, Jarkat cells, etc. In one embodiment, the nucleic acid encodes a GAL-4 binding site, the first chimeric protein comprises a GAL-4 nucleic acid binding protein and a beta catenin or a Tcf, and the second chimeric protein comprises a VP-16 and beta catenin or a Tcf (e.g. Tcf4).

In still another embodiment this invention provides vertebrate, preferably mammalian cells comprising one or more constructs of this invention. In one embodiment the cell is a cell comprising a nucleic acid encoding a peptide binding site and an effector gene, a first chimeric protein comprising a nucleic acid binding protein that binds the peptide binding domain where the nucleic acid binding protein is attached to the metabolic product or to a ligand that binds to the metabolic product; and a second chimeric protein comprising an expression control protein attached to the metabolic product or to the ligand that binds to the metabolic product such that when the first chimeric protein comprises said metabolic product, the second chimeric protein comprises the ligand and when said first chimeric protein comprises the ligand, the second chimeric protein comprises the metabolic product. Expression control proteins, first and second nucleic acids, effector genes, nucleic acid binding domains, include, but are not limited to those described above.

In still another embodiment this invention provides a nucleic acid selected from the group consisting of: a nucleic acid encoding a chimeric protein comprising a nucleic acid binding domain attached to a Tcf or to a beta catenin, and a nucleic acid encoding a transactivator attached to a beta catenin or to a Tcf. Particularly preferred nucleic acids include a nucleic acid encoding a nucleic acid binding protein attached to a Tcf4, a nucleic acid encoding a nucleic acid binding protein attached to a beta catenin, a nucleic acid encoding a Tcf4 attached to a transactivator, and a nucleic acid encoding a beta catenin attached to a transactivator (e.g. VP16). Preferred nucleic acids include DNAs or RNAs and in certain embodiments, the nucleic acid comprises a vector.

In still another embodiment this invention provides a kit for screening for an agent that modulates the ability of a cell to accumulate or to degrade a metabolic product. Preferred kits comprise a container containing a mammalian cell comprising a nucleic acid encoding a protein binding site and an effector gene; a first chimeric protein comprising a nucleic acid binding protein that binds said peptide binding domain attached to said metabolic product or to a ligand that binds to said metabolic product; a second chimeric protein comprising an expression control protein attached to said metabolic product or to said ligand that binds to said metabolic product such that when said first chimeric protein comprises said metabolic product, said second chimeric protein comprises said ligand and when said first chimeric protein comprises said ligand, said second chimeric protein comprises said metabolic product.

In another embodiment, the kit a container containing a nucleic acid as described herein.

Also provided are kits for selectively killing a cell. Such kits include a container containing a two-hybrid system component selected from the group consisting of one or more nucleic acids as described herein, and/or one or two chimeric proteins as described herein.

Definitions.

A "chimeric molecule" is a molecule comprising two or more molecules typically found separately in their native state that are joined together typically through one or more covalent bonds. The molecules may be directly joined or joined through a linker. Where the molecules are both polypeptides they may be joined through a peptide bond or a peptide linker forming a fusion protein.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

A "spacer" or "linker" as used in reference to a fusion protein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "spacer" or "linker" as used in reference to a chemically conjugated chimeric molecule refers to any molecule that links/joins the constituent molecules of the chemically conjugated chimeric molecule.

The "metabolic product" refers to a molecule formed as an intermediate or an end product of a metabolic pathway. The term may also include such products as they may be subsequently modified by member of a different pathway in a cell. When used as a domain of a chimeric molecule in this invention the metabolic product may be a full-length/full-size metabolic product or a fragment thereof sufficient to be specifically bound by another molecule.

The phrase "kill or inhibit a cell" refers to the death of a cell or a decrease in cellular growth and/or proliferation.

The term "specifically binds", when referring to the interaction of a nucleic acid binding protein and a nucleic acid binding site or two proteins or other binding pairs refers to a binding reaction which is determinative of the presence of the one or other member of the binding pair in the presence of a heterogeneous population of molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, etc. The binding may be by one or more of a variety of mechanisms including, but not limited to ionic interactions, covalent interactions, hydrophobic interactions, van der Waals interactions, etc.

The terms "binding partner", or a member of a "binding pair", or "cognate ligand" refers to molecules that specifically bind other molecules to form a binding complex such as antibody/antigen, lectin/carbohydrate, nucleic acid/nucleic acid, receptor/receptor ligand (e.g. IL-4 receptor and IL-4), avidin/biotin, etc.

The term ligand is used to refer to a molecule that specifically binds to another molecule. Commonly a ligand is a soluble molecule, e.g. a hormone or cytokine, that binds to a receptor. The decision as to which member of a binding pair is the ligand and which the "receptor" is often a little arbitrary when the broader sense of receptor is used (e.g., where there is no implication of transduction of signal). In these cases, typically the smaller of the two members of the binding pair is called the ligand. Thus, in a lectin-sugar interaction, the sugar would be the ligand (even if it is attached to a much larger molecule, recognition is of the saccharide).

The term "two-hybrid system" refers to a system comprising two chimeric molecules one of which bears a nucleic acid binding region, the other of which bears an expression control element (e.g. a transactivation or repressor domain). The molecules further a cognate binding pair such that one chimeric molecule is capable of specifically binding to the other chimeric molecule. The two-hybrid system further comprises a nucleic acid encoding a protein binding site that is specifically bound by the protein binding domain on the chimeric molecule thereby anchoring the chimeric molecule to the nucleic acid. The domain of the chimeric molecule recognizes and binds to its cognate binding partner on the second chimeric molecule thereby recruiting that molecule to the nucleic acid whereby the expression control element alters (e.g. activates) expression of a gene or cDNA comprising the underlying nucleic acid.

The phrase "one or more components of the two-hybrid systems of this invention" refers to either or both of the chimeric molecules comprising the two-hybrid system and/or the nucleic acid(s) encoding them and/or the nucleic acid comprising the protein recognition site and effector.

"Transfection" is used herein to mean the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell, including without limitation, both transient expression and stable expression.

"Delivery" is used to denote a process by which a desired compound is transferred to a target cell such that the desired compound is ultimately located inside the target cell or in, or on the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem*. 35:3800; Sprinzl et al. (1977) *Eur. J. Biochem*. 81: 579; Letsinger et al. (1986) *Nucl. Acids Res*. 14: 3487; Sawai et al. (1984) *Chem. Lett*. 805, Letsinger et al. (1988) *J. Am. Chem. Soc*. 110: 4470;

and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92:6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

A "recombinant expression cassette" or simply an "expression cassette" is a nucleic acid construct, generated recombinantly or synthetically, with nucleic acid elements that are capable of effecting expression of a gene or cDNA in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein.

The terms "gene" and "cDNA" are typically used interchangeably herein. Thus, for example, a reporter gene can comprise a genomic nucleic acid (e.g., comprising introns and exons) or a cDNA. In certain instances, the terms genomic DNA and cDNA will not be used interchangeably. This may be determined from the context of the usage.

An "apoptosis inducing gene" refers to a gene or cDNA implicated in apoptosis. Preferred apoptosis genes induce or increase apoptosis when they are activated. Apoptosis inducing genes include, but are not limited to P53, P73, Bax, Bad, FADD, caspases, etc.).

A method of "selectively killing" refers to a method that induces death of a particular cell type more frequently and/or sooner than the death of a different cell type (e.g. a cell lacking the particular distinguishing feature(s)) of the "targeted" cell.

The term "transactivator" refers to a molecule that induces transcription and/or upregulates transcription of a gene or cDNA. The transactivator may be a complete "native" molecule or a domain of a molecule that is capable of inducing and/or upregulating transcription of a gene or cDNA.

An "expression control domain" or "expression control protein" is typically a polypeptide that alters the expression of a gene or cDNA. Typical expression control proteins are transactivators (that upregulate expression of a gene or cDNA) or repressors (that downregulate the expression of a gene or cDNA).

A "cytotoxin" is an agent (e.g. a protein) that kills a cell.

An "apoptosis gene" refers to a gene whose expression is involved in an apoptosis pathway. Such apoptosis genes include, but are not limited to P53, P73, Bax, Bad, FADD, a a caspase gene, etc.

The term "test agent" refers to any agent that is to be screened for a desired activity. The "test composition" can be any molecule or mixture of molecules, optionally in a suitable carrier.

The term "small organic molecule" typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

An "effector molecule" is any molecule whose expression is to be controlled by the two-hybrid system of this invention. Suitable effector molecules include, but are not limited to cytotoxins, reporter genes, enzymes, apoptosis genes, and the like.

"Reporter genes" are genes or cDNAs that express an easily assayable (detectable and/or quantifiable) product. Detection of the assayable product indicates the expression and/or level of expression of the reporter gene. Reporter genes are well known to those of skill in the art. They include, but are not limited to, genes expressing bacterial chloramphenicol acetyl transferase (CAT), beta-galactosidase (β-gal), green fluorescent protein (GFP) and other fluorescent proteins, various bacterial luciferase genes, e.g., the luciferase genes encoded by *Vibrio harveyi*, *Vibrio fischeri*, and *Xenorhabdus luminescens*, the firefly luciferase gene FFlux, and the like.

The term "modulate" when used with reference to the ability of a cell to accumulate or to degrade a metabolic product.

The terms "peptide binding site" or "protein binding site" refer to a nucleic acid sequence that is recognized and/or bound by a nucleic acid binding protein (e.g. a DNA binding protein).

A "nucleic acid binding domain" refers to a protein or a region of a protein that recognizes and/or binds to a nucleic acid. A nucleic acid binding protein (e.g., a DNA binding protein) can be a full-length nucleic acid binding protein or a fragment thereof that binds to a nucleic acid.

The term "kit" refers to a collection of materials, more preferably a packaged collection of materials (preferably related materials) to perform a particular function (e.g. to run a screening assay, to express a protein, to culture a cell, etc.). A kit may optionally comprise instructional materials describing the use of the materials present in the kit.

BRIEF DESCRIPTION OF THE DRAWINGS

FIG. 2A shows the structure of the two-hybrid components. The pBIND/WT-β-catenin plasmid is designed to produce chimera protein that consists of yeast GAL4 DNA binding domain and wild type-β-catenin. The pBIND/MT-β-catenin plasmid is designed to produce the chimera protein consists of GAL4 DNA binding domain and the GSK-3β phosphorylation site (aa29-aa48)-deleted β-catenin. The pACT/FL-Tcf4 plasmid is designed to produce the chimera protein consists of herpes simplex virus VP16 transcription activation domain and full length Tcf4. The pACT/DN-Tcf4 plasmid is designed to produce the chimera protein consists of VP16 transcription activation domain and β-catenin binding site (aa2-aa53)-deleted Tcf4. FIG. 2B illustrates expression of GAL4/β-catenin and VP16/Tcf4 in SW480 Cells. Cells were transfected with pBIND/β-catenin or pACT/Tcf4 plasmid and cultured for 24 h. Then expression levels of fusion proteins were detected by western blot. FIG. 2C illustrates the specificity of two-hybrid system. SW480 cells were transfected with various combinations of GAL4 fusion protein, VP16 fusion protein and pG5/luc plasmids and cultured for 24 h. Luciferase activity of each sample was measured by luminometer.

FIG. 3A illustrates APC dependent selective expression of the two-hybrid output gene in SW480 cells. SW480 cells were transfected with various concentration of the pcDNA/APC plasmid in the presence of pBIND/WT or MT-β-catenin plasmid, pACT/FL-Tcf4 plasmid and pG5/luc plasmid. After 24 h culture, cells were lysed and luciferase activity was measured. FIG. 3B illustrates detection of two-hybrid component proteins in SW48 cells. SW480 cells were transfected with various concentration of the pcDNA/APC plasmid in the presence of pBIND/WT or MT-β-catenin plasmid, pACT/FL-Tcf4 plasmid and pG5/luc plasmid. After 24 h culture, cells were lysed and two-hybrid component proteins were detected by western blotting.

FIG. 4A shows the expression levels of cytoplasmic β-catenin and APC in human cell lines. SW480 cells, SW48 cells, U-20S cells and 293 cells ($1.0 \times 10^6$ cells) were lysed with TE buffer containing protease inhibitors (complete mini, Boehringer Mannheim), and soluble fraction was collected by centrifugation. Each sample was loaded to 4-20% gradient acrylamide gel and transferred to nitrocellulose membrane. Separated protein was detected with anti-β-catenin antibody or anti-APC antibody. FIG. 4B illustrates detection of GAL4 fusion protein degradation products. SW480 cells and SW48 cells were transfected with pBIND/WT or MT-β-catenin plasmid and cultured for 24 h. Cells were lysed with SDS-page sample buffer and loaded to 4-20% gradient poly acrylamide gel. Separated protein was transferred to nitrocellulose membrane and GAL4 protein was detected with anti-GAL4 antibody. FIG. 4C shows selective output gene expression of two-hybrid system dependent on the APC profile of the cell lines. Human cell lines were transfected with various concentrations of pBIND/WT-β-catenin plasmid in the presence of pACT/FL-Tcf4 and pG5/luc plasmids. Lucifease activity of each point was measured after 24 h culture.

FIG. 5A shows activation of p53 responsive-luciferase expression by p53-EGFP. The pcDNA/p53-EGFP was transfected with p53-Luc, pAP-1-Luc or pCRE-Luc (Stratagene) in the presence of pRL/TK (Promega) to SW480 cells and cultured for 24 h. Cells were harvested and luciferase activity was measured. FIG. 5B illustrates detection of p53-EGFP in SW480 cells. SW480 cells were co-transfected with pBIND/WT-β-catenin, pACT/FL-Tcf4 and pG5/p53-EGFP and cultured for 24 h. Produced p53-EGFP was detected by western blot using anti-p53 antibody. FIG. 5C shows the results of a cell killing experiment using two-hybrid system. SW480 cells were transfected with pBIND/WT-β-catenin, pACT/FL-Tcf4 and pG5/p53-EGFP, and cultured for 48-72 h. Cells were trypsinized and washed with PBS. Then, cells were suspended in PBS containing 10 μM propydium iodide. Cell death profile of EGFP positive cells were analyzed by measuring the uptake of propydium iodide using flow cytometer.

DETAILED DESCRIPTION

This invention provides novel approaches to the treatment (e.g. amelioration of one or more symptoms) of pathological states characterized by the undesired accumulation of one or more metabolic products. In addiction, this invention provides effective systems in which to screen for agents that modulate the ability of a cell to degrade or accumulate a metabolic product (e.g. β-catenin).

In general the methods of this invention utilize a two-hybrid system, more preferably a mammalian two-hybrid system (e.g. Promega Check Mate™). A cell is provided containing constructs forming a two-hybrid system. The first construct comprises a first chimeric protein comprising having a nucleic acid binding domain attached to either the metabolic product that accumulates, an enzyme in the metabolic pathway that produces or degrades the metabolic product, or to a ligand that binds to the metabolic product of to the enzyme. A second construct is provided that is a chimeric protein comprising a transactivating domain attached to a cognate binding partner of the metabolic product, ligand, or enzyme component of the first construct. Thus, for example, where the first construct comprises the metabolic product attached to the nucleic acid binding domain, the second construct comprises a ligand that binds the metabolic product attached to a transactivating domain. A third construct in the cell is a nucleic acid comprising a nucleic acid sequence capable of being bound by the nucleic acid binding domain of the first construct and a gene/cDNA encoding an effector. The effector is any nucleic acid or protein whose transcription and/or translation is to be regulated by this two-hybrid system. Thus, for example, in certain preferred embodiments the effector is a reporter or a cytotoxin.

In a cell that has a reduced ability or no ability to degrade the metabolic product, the construct bearing the metabolic product specifically binds to the construct bearing the cognate binding partner of that product. The two-protein complex is anchored to the nucleic acid by the component bearing the nucleic acid binding domain and the attached transactivator domain upregulates (or in some embodiments, down-regulates) expression of the effector gene. Where the cell is able to degrade the metabolic product, the construct bearing that product is all, or partially, degraded. No complex is formed between the two constructs transcription and/or translation of the effector gene is unaffected (e.g. there is no signal).

Figure 1:
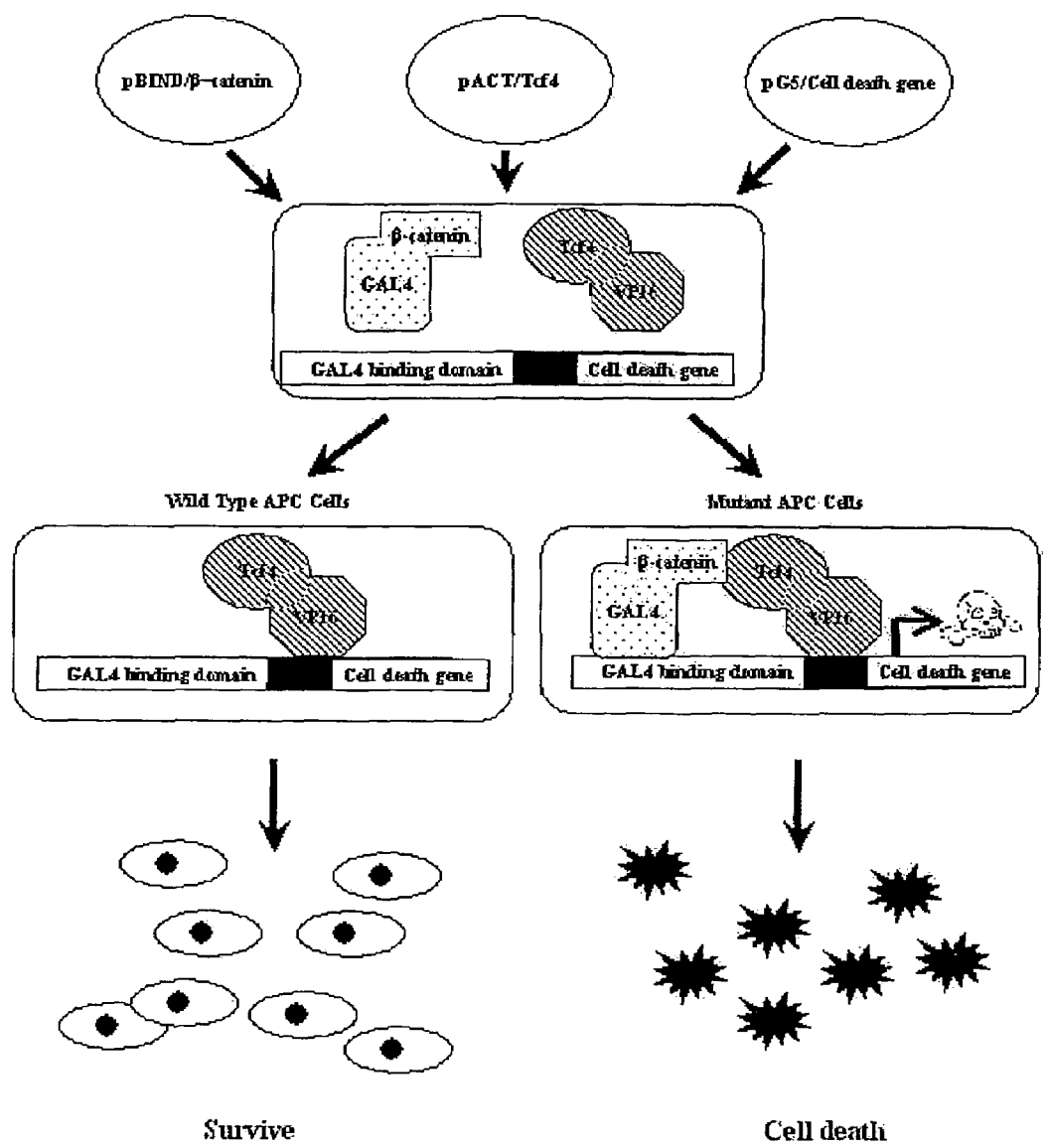
FIG. 1 illustrates the concept of gene therapy using β-catenin/Tcf4 mammalian two-hybrid system. When cells are transfected with the plasmids encoding GAL4/WT-β-catenin, VP-16/FL-Tcf4 and GAL4-responsive element-driven suicide gene, suicide gene expression occurs only in APC mutated cells.

One specific embodiment of this system is illustrated in FIG. 1 which pertains to functional loss of the Adenomatous Polyposis Coli (APC) gene product originally discovered in familial Adenomatous Polyposis patients (and also found in varieties of sporadic cancers including colon cancer). The tumor suppressor APC gene product is a member of the Wnt signaling pathway. This pathway is believed to play a critical and evolutionarily conserved role in directing cell fates during embryogenesis. In addition, inappropriate activation of the Wnt signal transduction pathway plays a role in a variety of human cancers.

Wnt signaling is regulated by the presence or absence of the intracellular protein β-catenin. A large multiprotein machine that includes proteins of the APC and Axin families normally facilitates the addition of phosphate groups to β-catenin by glycogen synthase kinase-3β (GSK3β). Phosphorylated β-catenin binds to a protein called βTrCP and is then modified by the covalent addition of a small protein called ubiquitin. Proteins tagged with ubiquitin are normally degraded by the proteosome.

Mutated APC is unable to form an APC/Axin complex. In this case, the β-catenin is not phosphorylated and ultimately not degraded. Thus, β-catenin accumulates in the cell. The excess β-catenin accumulates and enters the nucleus, where it finds a partner, e.g., a DNA binding protein of the TCF/LEF family. Together they activate new gene expression programs, e.g. oncogenic target genes such as cyclin D1. This condition is observed in a large number of cancers (e.g. in 80 to 85% of all colon cancers).

In one embodiment, the methods of this invention are used to selectively kill cells having a defective APC or to screen for modulators of the Wnt pathway leading to β-catenin degradation. A specific embodiment is illustrated in FIG. 1, which shows a first chimeric molecule comprising a nucleic acid binding domain, in this case Gal4 attached to a β-catenin. A second chimeric molecule comprises a T-cell factor (e.g., Tcf-4) attached to a transactivator (VP16). The third construct is a nucleic acid encoding a Gal4 binding domain and an effector (e.g. a thymidine kinase) gene.

A cell having a defective APC will accumulate β-catenin, in this case, the Gal4-β-catenin construct. The Gal-4-β-catenin construct binds to the Gal4 binding site on the nucleic acid. The Tcf4-VP16 chimeric molecule binds to the β-catenin via the β-catenin/Tcf4 interaction thereby juxtaposing the VP16 transactivator to the nucleic acid which then induces transcription of the effector gene. If the effector gene is a cytotoxin the cell having a defective APC is killed. If the effector is a reporter the resulting signal identifies the cells a cell comprising a defective APC. Where the cell is contacted with a test agent and the effector is a reporter, a change in signal indicates that the test agent modulates activity of the Wnt pathway in particular with respect to the accumulation of β-catenin.

A cell having a normal APC will degrade β-catenin (in this case the Gal4-β-catenin chimeric molecule. The Tcf4-VP16 chimeric molecule then is not directed to the nucleic acid and there is no alteration in expression (or non-expression) of the effector gene. Thus, where the effector gene is a cytotoxin, a cell having normal APC and therefore able to degrade β-catenin will not express the cytotoxin and will not be killed. The use of this system with a cytotoxic effector thus specifically eliminates cells having a defective APC.

I. Uses of the Methods of this Invention

The above-described system, or variants thereof, can be used in a wide variety of contexts to screen for agents (e.g. drugs or lead compounds) that modulate (e.g. increase or decrease) the ability of a cell to accumulate or to degrade a metabolic product. In other embodiments the methods described herein can be used to selectively kill or inhibit cells that abnormally accumulate or degrade metabolic products and thereby mitigate symptoms of pathological states characterized by the abnormal accumulation or degradation of metabolic products.

A) Screening for Modulators of the Ability of a Cell to Accumulate or to Degrade Metabolic Products As indicated above, the methods of this invention are well suited to screening for an agent or agents that modulate the ability of a cell to accumulate or to degrade a metabolic product. In preferred embodiments, such assays involve providing a cell, as described above, containing the two chimeric proteins (binding-domain/metabolite, ligand-transactivator) and the nucleic acid comprising an effector. In one embodiment, the effector preferably encodes a reporter gene or another gene that encodes a detectable, but not lethal product. In this instance, the gene expression is detected. In another embodiment, the gene encodes a lethal gene product (e.g. P53 or a cytotoxin) and the assay involves measuring the number of viable cells.

The cell is then contacted with the agent or agents of interest and activity of the reporter gene is detected. Where the reporter gene shows an expression level and/or activity level different that the level shown in a cell of the same type harboring the same constructs, but contacted with a different concentration of test agent (or no test agent), the test agent is presumed to have altered the metabolic pathway leading to the accumulation or degradation of the metabolic product.

The effect of the test agent can be direct, e.g. by binding or degradation of the metabolic product or an enzyme or other ligand that normally binds to the metabolic product, or the effect can be indirect, e.g. by binding, degrading, or otherwise altering a different component of the pathway that ultimately alters the ability of the cell to accumulate or to degrade the metabolic product of interest. Thus, for example, in the case of the APC system described above, the test agent may alter the cells accumulation of β-catenin directly by binding to or otherwise interacting with APC, axin, or with Tcf. Alternatively, the test agent may act indirectly, for example, by altering the phosphorylation of β-catenin by binding to or otherwise altering the activity of GSK3β. This is, of course, only one illustrative mechanism for indirect action by a possible test agent and numerous other possibilities also exist. In this example, regardless of the mechanism of action of the test agent, as long as it alters the accumulation or degradation of β-catenin, its activity will be detected in the assays of this invention.

1) Scoring the Assay

The assays of this invention are scored according to standard methods well known to those of skill in the art. Typically the expression level of the reporter gene is assayed according to standard methods. Reporter genes are genes or cDNAs that express an easily assayable (detectable and/or quantifiable) product. Detection of the assayable product indicates the expression and/or level of expression of the reporter gene. Reporter genes are well known to those of skill in the art. They include, but are not limited to, genes expressing bacterial chloramphenicol acetyl transferase (CAT), beta-galactosidase (β-gal), green fluorescent protein (GFP) and other fluorescent proteins, various bacterial luciferase genes, e.g., the luciferase genes encoded by *Vibrio harveyi*, *Vibrio fischeri*, and *Xenorhabdus luminescens*, the firefly luciferase gene FFlux, and the like. The reporter gene can be the sole gene under the control of the promoter activated or inhibited by the transcription factor (e.g. VP-16)

comprising the "second chimeric molecule) or there may be one or more other genes also under control of the subject promoter (e.g. P53-eGFP).

The assays of this invention are not limited to the use of reporter genes. Generally the transcription, translation, or activity of any gene or cDNA can routinely be detected. Thus, for example, the transcribed mRNA can be detected by methods including, but not limited to, Northern blots, amplification techniques (e.g. PCR), and the like. Similarly, the translated protein product can be detected by detecting the characteristic activity of the protein or by detecting the protein product itself (e.g. via Western blot, capillary electrophoresis, and the like).

As indicated above, in preferred embodiments, the expression of the "reporter" gene or cDNA is evaluated with respect to one or more controls. Typical embodiments utilize a negative control comprising the test agent(s) at a lower concentration or in the absence of the test agent(s). A difference in expression of the "reporter" gene in the presence of the test agent(s) as compared to the expression of the reporter gene where the test agent is present at a lower concentration or absent indicates that the test agent has an activity on the metabolic pathway being assayed.

Other embodiments, may utilize a positive control comprising a cell administered the test agent or, more preferably, a reference agent at a particular concentration. The effect of the test agent is then measured relative to the particular concentration of test agent or reference agent.

Still other controls may be utilized to assay for the specificity of the activity of the test agent. Thus, for example the test agent may act thorough generalized activity of the cell (e.g. by diminishing metabolic rate, cell viability, proliferation rate, growth rate, etc.) rather than through specific activity on the pathway of interest. In preferred embodiments it is desired to distinguish between generalized activity of the test agent(s) and specific activity on the metabolic pathway of interest. In certain embodiments, this is accomplished by expressing one or both of the chimeric proteins under control of an inducible promoter. Thus, for example, the Gal4-β-catenin chimera may be under control of a inducible promoter (e.g., ecdysone inducible system or tetracycline inducible system). If the test agent still has an effect in the absence of induced Gal4-β-catenin or if varying the level of induction of Gal4-β-catenin does not alter the effect of the test agent(s) then the test agent(s) are presumed to act through a non-specific mechanism. Conversely, where altering the expression level of Gal4-β-catenin alters the apparent activity of the test agent(s) the agent(s) are presumed to act specifically on the pathway of interest (in this example, the Wnt signaling pathway).

The assays of this invention are typically scored as positive where there is a difference between the activity seen with the test agent present and the (usually negative) control, preferably where the difference is statistically significant (e.g. at greater than 80%, preferably greater than about 90%, more preferably greater than about 98%, and most preferably greater than about 99% confidence level). Most preferred "positive" assays show at least a 1.2 fold, preferably at least a 1.5 fold, more preferably at least a 2 fold, and most preferably at least a 4 fold or even a 10-fold difference from the negative control.

2) Agents for Screening: Combinatorial Libraries (e.g., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487-493, Houghton et al. (1991) *Nature*, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random biooligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309-314), and PCT/US96/10287), carbohydrate libraries (see, e.g., Liang et al. (1996) *Science*, 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506, 337, benzodiazepines U.S. Pat. No. 5,288,514, and the like).

Devices for the preparation of combinatorial libraries are commercially available (see, e.g., 357 MPS, 390 MPS, Advanced Chem Tech, Louisville K.Y., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and, the Venture™ platform, an ultra-high-throughput synthesizer that can run between 576 and 9,600 simultaneous reactions from start to finish (see Advanced ChemTech, Inc. Louisville, K.Y.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, MO., ChemStar, Ltd, Moscow, RU, 3D Pharmaceuticals, Exton, PA., Martek Biosciences, Columbia, MD., etc.).

3) High Throughput Screening

Any of the assays for compounds modulating the accumulation or degradation of metabolic products described herein are amenable to high throughput screening. Preferred assays detect increases or decreases in the transcription and/or translation of a reporter gene in response to the presence of a test compound.

The cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

B) Selectively Killing or Inhibiting Cells Showing an Abnormality in a Metabolic Pathway The methods of this invention can also be used to selectively kill or inhibit a cell showing an abnormality in a metabolic pathway. This is accomplished simply by using a cytotoxic gene or cDNA as the effector. Cells able to degrade the metabolic product in question (e.g. β-catenin) will also degrade the metabolic product producing the chimeric molecule and the effector gene will not be transactivated. Conversely, cells unable to degrade the metabolic product will have a functioning two-hybrid system that transactivates the cytotoxic effector thereby killing or inhibiting the cell. The method is thus highly selective for cells showing an abnormality in the metabolic pathway of interest.

It is noted that this approach is not only useful in the treatment of traditional "diseases of accumulation", but also in the treatment of various cancers characterized by the accumulation of a metabolic product.

As used herein, a cytotoxic gene or cDNA refers to a gene or cDNA that when expressed results in cell death or renders the cell susceptible to killing by another reagent. Thus, for example, expression of a herpes virus thymidine kinase gene will render a cell susceptible to the drug gangcyclovir which will cause the selective killing of any cell producing tk.

Suitable cytotoxic genes include, but are not limited to genes for cytotoxins such as *Psuedomomas exotoxin, Diphtheria* toxin, ricin, abrin, thymidine kinase, apoptosis genes, and genes involved in an apoptosis related pathway (e.g. P53, P73, Bax, Bad, FADD, caspases, etc.). In certain embodiments, the gene is an anti-apoptotic gene such as Bcl2 or MDM2, etc.

In Example 1 herein, the method is illustrated for the selective killing of cells having a defective APC. A two-hybrid system comprising Gal4-β-catenin and Tcf-VP16 chimeric molecules is used to transactivate an effector comprising a P53 or a tk gene. As illustrated in the Example, the method provides highly specific killing of APC-defective cells.

The method is not limited to the in vitro use. To the contrary, the chimeric molecules, or nucleic acids comprising the chimeric molecules, can be delivered to cells in vivo (e.g. using gene therapy delivery methods as described herein) where they provide highly effective killing of the defective cell(s). The methods thus offer a means to treat a large number of cancers and other diseases of accumulation.

C) Selectively Compensating for Metabolic Defects

Instead of killing the subject cells, the methods of this invention can also be used to selectively compensate for one or more metabolic defects. In this instance, the effector is a gene or cDNA that encodes the protein (e.g. an enzyme) for which the cell is deficient. When the two-hybrid system is inserted into a cell that is deficient for the desired activity, the two-hybrid system turns on the effector thereby initiating the desired metabolic activity (e.g. degrading the particular metabolic product).

D) Illustrative Pathologies Suitable for Intervention using the Methods of this Invention The methods of this invention can be used to assay for agents having activity in essentially any condition characterized by the accumulation of a metabolic product. Similarly, the methods can be used to selectively kill cells that show a degradation defect. Thus, the methods of this invention are useful in the treatment of diseases of accumulation or in screening for agents that are also useful in the treatment of diseases of accumulation.

Diseases of accumulation (storage diseases) are well known to those of skill in the art and include, but are not limited to Storage disease include but are not limited to glycogen storage disease I, GM1 gangliosidoses, MPS IV B (Morquio B), GM2 gangliosidoses (O, B, AB, B1 variants), Niemann-Pick disease (A, B, and C), metachromatic leukodystrophy (arylsulfatase A and SAP-1 deficient), Krabbe disease, Fabry disease, Gaucher disease, Farber disease, Wolman disease (cholesterol ester storage disease), MPS I (Hurler and Scheie syndromes), MPS II (Hunter syndrome), MPS III A, C, and D (Sanfilippo A, C, and D), PS III B (Sanfilippo B), MPS IV A (Morquio A), MPS VI (Maroteaux-Lamy syndrome), MPS VII (beta-glucuronidase deficiency), Multiple sulfatase deficiency, Mucolipidosis I (Sialidosis), Mucolipidosis II & III, alpha-Mannosidosis, beta-Mannosidosis, Fucosidosis, Sialic acid storage disease, Galactosialidosis, Aspartylglucosaminuria Cystinosis.

The etiology of such storage diseases is relatively well understood. Thus, identification of metabolic product(s) and ligands for use in two-hybrid system relevant to the disease is relatively straightforward. For example, in Gauchers disease defective genes for glucocerbrosidase result in the accumulation of glucosylceramide in macrophages. Use of the two-hybrid system of this invention with glcosylceramide, or another component of the same pathway with an effector that is a cytotoxin will selectively kill cells showing the Gauchers phenotype, while use of an effector that is a glucocerbrosidase selectively replaces the missing activity in those cells in need of such activity. Similarly, Krabbe disease is a lethal demelinating condition caused by a deficiency of galactosylceramidase (GALC) enzyme activity. This leads to accumulation of cerebroside and psycosine. Use of either metabolic product in a two-hybrid system and galactosylceramidase enzyme as the effector, according to the methods of this invention provides a system that selectively replaces the desired metabolic activity in cells in need of such activity.

The methods of this invention are also useful in the treatment of a number of cancers or for screening for therapeutic agents useful in the treatment of a number of cancers. For example defective APC is observed in a large number of cancers (e.g. in 80 to 85% of all colon cancers). In addition, viral activation of Wnt-1 causes mammary tumors in mice and mutations that make β-catenin refractory to destruction are found in a wide variety of cancers (see, e.g., Polakis (1999) *Curr. Opin. Gene. Dev.*, 9: 15).

II. Components of the Methods of this Invention

A) The First and Second Chimeric Molecules

The methods of this invention utilize a mammalian two-hybrid system involving a first chimeric molecule having a nucleic acid binding domain and a second chimeric molecule having a regulatory domain (e.g. a transactivator or a repressor). The first chimeric molecule preferably comprises a domain that is the metabolic product of interest (e.g. β-catenin) while the second chimeric molecule comprises a domain that is a ligand, enzyme, etc. that binds the metabolic product domain comprising the first chimeric molecule. The ligand and the metabolic product are interchangeable. That is, the first chimeric molecule may comprise the ligand and the second chimeric molecule may comprise the metabolic product.

In the APC system illustrated in example 1, the first chimeric molecule comprises a Gal4 domain and a β-catenin domain, while the second chimeric molecule comprises a Tcf4 domain and a VP16 domain. The components can be reversed, so the first chimeric molecule comprises Gal4 and Tcf4, while the second chimeric molecule comprises β-catenin and VP16. In addition, the ligand need not be Tcf4. Essentially any molecule in the Wnt pathway that binds to β-catenin is suitable. Thus, for example, Tcf4 may be substituted with Tcf1, Tcf3, Lef1, or other members of the Tcf family. Other molecules involved in the Wnt signaling pathway include, but are not limited to axin, disheveled, GSK3β, β-TrCP, casein kinases 1ϵ and II, protein phosphatase 2A, and FRAT (frequently rearranged in advanced T cell lyphomas).

The two-hybrid systems used in this invention thus comprise: 1) A metabolic product (or fragment thereof), 2) A ligand that binds to the metabolic product or fragment thereof, 3) A regulatory (expression control) domain, and 4) A nucleic acid binding domain. The nucleic acid binding domain and the regulatory domain are on different chimeric molecules.

1) The Metabolic Product

Selection of the metabolic product (or fragment thereof) for use in the two-hybrid system according to the methods of this invention is a function of the particular metabolic pathway or pathology of interest. As illustrated in example 1, one metabolic product useful for the Wnt signaling pathway is β-catenin.

In the case of Gaucher's disease which is characterized by the inactivation of glucocerebrosidase resulting in the accumulation of glucosylceramide in macrophages, glucosylceramide or the glucocerebrosidase provide effective targets (metabolic products or enzymes) for use in the methods of this invention. Similarly, Krabbe's disease, a lethal demyelinating condition is caused by a deficiency of galactosylceramidase (GALC) enzyme activity leading to the accumulation of cerebroside and psychosine. Again, both the accumulated metabolic products and/or the deficient enzyme and/or other molecules in the same metabolic pathway provide good targets for use in the methods of this invention.

Using the teaching provided herein, one of skill may readily determine other metabolic products for use in the two-hybrid systems for assays and therapeutics according to the methods of this invention.

2) The Ligand that Binds to the Metabolic Product

The ligand that binds the metabolic product may be a naturally occurring molecule found in the metabolic pathway that produces or degrades the metabolic product. Alternatively, the ligand used to bind the metabolic product of interest need not be a ligand found in the pathway that normally produces the metabolic product. Any ligand that binds the metabolic product, and more preferably that specifically binds the metabolic product is suitable. Thus, for example the system illustrated in example 1 utilizes a member of the TCF/LEF family. The TCF family members are known to bind to β-catenin, but are not believed to be participants in the pathway that produces or degrades β-catenin.

The ligand need not even be a naturally-occurring molecule. Thus, for example, where a ligand is needed for a particular molecule (e.g. glucosylceramide in Gaucher's disease), one can be readily generated using any of a number of known technologies (e.g. phage display or other methods of directed evolution. The use of phage display libraries to identify single chain polypeptides that specifically bind a particular molecule with high affinity is well known to those of skill in the art (see, e.g., McCafferty et al. (1990) *Nature*, 348: 552-554; Hoogenboom et al. (1991) *Nucleic Acids Res*. 19: 4133-4137; Marks et al. (1991) *J. Mol. Biol*. 222: 581-597; Marks et al. (1993). *Bio/Technology*, 10: 779-783; Griffiths et al. (1993) *EMBO J*. 12: 725-734; Clackson et al. (1991) *Nature*. 352: 624-628).

3) The Expression Control Protein/domain

One of the chimeric molecules used in the two-hybrid systems of this invention comprises an expression control (regulatory) domain. The expression control domain is typically a polypeptide that alters the expression of a gene or cDNA. Typical expression control proteins are transactivators (that upregulate expression of a gene or cDNA) or repressors (that downregulate the expression of a gene or cDNA).

While in one particularly preferred embodiment, the expression control protein is VP16, in preferred embodiments, any TATA box binding domain of a known transactivating protein can replace VP16. Other suitable transactivators will be known to those of skill in the art. Various transactivators include, but are not limited to, E2F4 (U.S. Pat. No. 6,045,999), human transcription factor (see U.S. Pat. No. 4 6,001,971), transcription factor Islet-Brain 1 (IB1) (U.S. Pat. No. 5,880,261), TFIIB transcription factor from *Candida albicans* (U.S. Pat. No. 5,863,762), DPI (U.S. Pat. No. 5,863,757), DP-3 (U.S. Pat. No. 5,859,199), Liver enriched transcription factor (U.S. Pat. No. 5,849,485), RNA polymerase transcription factor (U.S. Pat. No. 5,792,634), transcription factor APRF (acute phase response factor) (U.S. Pat. No. 5,719,042), cell-type specific transcription factor (U.S. Pat. No. 5,710,025), p300 transcription factor (U.S. Pat. No. 5,658,784), human transcription factor IIA (U.S. Pat. No. 5,652,117), S-II transcription factor (U.S. Pat. No. 5,196,303), and the like.

While in preferred embodiments, this invention utilizes an expression control domain that is a transactivator, in certain embodiments, a control element is used that is a repressor of gene or cDNA transcription. Various transcription repressors are known to those of skill in the art. These include, but are not limited to Kruppel-like factor (U.S. Pat. No. 6,077,933), tetracycline repressor (U.S. Pat. Nos. 5,972,650 and 5,917,122), ETS2 repressor (U.S. Pat. No. 5,856,125), papillomavirus E2 transactivation repressor (U.S. Pat. No. 5,595,884), the CI434 repressor, plasmids (U.S. Pat. No. 5,147,789), and the like.

4) The Nucleic Acid Binding Domain

Virtually any nucleic acid binding protein or the binding domain therein may be used in the two-hybrid systems of this invention. The binding protein preferably binds to a particular nucleic acid sequences with sufficient affinity that an attached transactivator is able to upregulate expression of an appropriately positioned gene or cDNA. While the Gal4 domain provides a well characterized and particular preferred embodiment, many other nucleic acid binding molecules are known to those of skill in the art. For example, U.S. Pat. Nos. 6,010,849 and 5,578,444 provide assays for the ready identification of (typically non-protein) nucleic acid binding molecules and also provide a number of illustrative molecules.

Other nucleic acid binding proteins comprise various transactivators and are often characterized by the presence of a zinc-finger motif. Suitable nucleic acid binding proteins and assays for identifying these and other nucleic acid binding proteins are well known to those of skill in the art. Thus, for example, U.S. Pat. No. 6,066,452 teaches methods for simultaneously selecting binding site sequences for multiple DNA binding proteins. U.S. Pat. No. 6,07,988 discloses method of designing zinc finger binding polypeptides for binding to a particular target sequence and lists a number of suitable zinc finger polypeptides. U.S. Pat. No. 5,773,583 discloses a number of "Egr" proteins that bind to specific DNA sequences.

Using the teaching provided herein, other suitable nucleic acid binding proteins/binding domains can be readily determined by one of ordinary skill in the art without undue experimentation.

5) Preparation of the Chimeric Molecules

The chimeric molecules comprising the two-hybrid systems of this invention may be chemically conjugated domains, or, where the domains are linked by an amino acid or peptide linker the chimeric molecules may be recombinantly expressed fusion proteins. Where the chimeric molecules are chemically conjugated, the chimeric molecule is delivered to the cell. Where the chimeric molecules are fusion proteins either the fusion protein itself is delivered to the cell or a nucleic acid encoding the fusion protein is transfected into the cell where it produces the desired fusion protein(s).

Means of chemically conjugating molecules are well known to those of skill. Polypeptides typically contain variety of functional groups; e.g., carboxylic acid (COOH) or free amine (—NH$_2$) groups, which are available for reaction with a suitable functional group on an effector molecule to bind the effector thereto. Alternatively, the components comprising the chimeric molecule(s) (e.g. Gal4 and β-catenin) may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the two domains of the chimeric molecule(s) to each other. In preferred embodiments, the linker is capable of forming covalent bonds to both the domains. Suitable linkers are well known to those of skill in the art and include, but are not limited to, straight or branched-chain carbon linkers, heterocyclic carbon linkers, or peptide linkers. In certain embodiments, the linkers may be joined to amino acids comprising the domains through their side groups (e.g., through a disulfide linkage to cysteine). However, in a preferred embodiment, the linkers will be joined to the alpha carbon amino and carboxyl groups of the terminal amino acids. The linker may be bifunctional, having one functional group reactive with a substituent on the first domain (e.g. Gal4) and a different functional group reactive with a substituent on the second domain (e.g. β-catenin). Alternatively, the two domains may be derivatized to react with a "mono-functional" linker (see, e.g., U.S. Pat. No. 4,671,958 and 4,659,839 for procedures to generate reactive groups on peptides).

In a particularly preferred embodiment, the chimeric molecules of this invention are fusion proteins. The fusion protein can be chemically synthesized using standard chemical peptide synthesis techniques, or, more preferably, recombinantly expressed. Where both molecules are relatively short the chimeric molecule may be chemically synthesized as a single contiguous polypeptide. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis*, 2 nd ed. Pierce Chem. Co., Rockford, Ill. (1984).

In a most preferred embodiment, the chimeric molecules of the present invention are synthesized using recombinant DNA methodology. Generally this involves creating a DNA sequence that encodes the fusion protein, placing the DNA in an expression cassette under the control of a particular promoter, and expressing the chimeric (fusion) protein in a host cell.

DNA encoding the fusion protein(s) used in the methods of this invention may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 to 500 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention is using DNA amplification methods such as polymerase chain reaction (PCR). Thus, for example, as illustrated in Example 1, a human β-catenin cDNA is PCR amplified with the BamHI linker and coned into a Bam HI site of pBIND. The human Tcf4 cDNA with Bam HI linker is PCR amplified and cloned into the Bam HI site of pACT.

A linker may be introduced into the chimeric molecules, e.g., between the nucleic acid binding domain and the metabolic product or between the ligand and the transactivator. The linker is used to separate the two domains comprising the chimeric molecule by a distance sufficient to ensure that, in a preferred embodiment, each domain properly folds into its secondary and tertiary structures. Preferred peptide linker sequences adopt a flexible extended conformation, do not exhibit a propensity for developing an ordered secondary structure that could interact with the functional GM-CSF and G250 domains. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Still other amino acid sequences that may be used as linkers are disclosed in Maratea et al. (1985), *Gene* 40: 39-46; Murphy et al. (1986) *Proc. Nat'l. Acad. Sci. USA* 83: 8258-62; U.S. Pat. No. 4,935,233; and U.S. Pat. No. 4,751, 180.

The length of the peptide linker sequence may vary without significantly affecting the biological activity of the fusion protein. In one preferred embodiment of the present invention, a peptide linker sequence length of about 2 amino acids is used to provide a suitable separation of functional protein domains, although longer linker sequences also may be used. The linker sequence may be from 1 to 50 amino acids in length. In the most preferred aspects of the present invention, the linker sequence is from about 1-20 amino acids in length. In the specific embodiments disclosed herein, the linker sequence is from about 2 to about 15 amino acids, and is advantageously from about 2 to about 10 amino acids. Peptide linker sequences not necessarily required in the fusion proteins of this invention.

Generally the linker will have no specific biological activity other than to join the proteins or to preserve some minimum distance or other spatial relationship between them. However, the constituent amino acids of the spacer may be selected to influence some property of the molecule such as the folding, net charge, or hydrophobicity.

Where it is desired to recombinantly express either of the two chimeric molecules comprising the two-hybrid systems of this invention, the G250, the GM-CSF, or the G250-GM-CSF fusion protein, the nucleic acid sequences encoding the desired protein are typically operably linked to suitable transcriptional or translational regulatory elements. The regulatory elements typically include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants may additionally be incorporated.

The nucleic acid sequences encoding the fusion proteins may be expressed in a variety of host cells, including *E. coli* and other bacterial hosts, and most preferably eukaryotic host cells including but not limited to yeast, insect cells, and mammalian cells. The recombinant protein gene will be operably linked to appropriate expression control sequences for each host.

The plasmids of the invention can be transferred into the chosen host cell by well-known methods such as calcium chloride transformation for *E. coli* and calcium phosphate treatment or electroporation for mammalian cells. In vivo transfection can be accomplished using standard gene therapy methods, e.g. as described herein.

Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2 nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077-1080; Van Brunt (1990) *Biotechnology*, 8: 291-294; Wu and Wallace, (1989) *Gene*, 4: 560; and Barringer et al. (1990) *Gene*, 89: 117.

C) The Nucleic Acid

The nucleic acid component of the two-hybrid systems of this invention is produced according to standard methods. Typically, the nucleic acid comprises a binding domain recognized by a nucleic acid binding molecule (e.g. GAL4) and an expression cassette comprising one or more genes or cDNAs. The expression cassette positioned with respect to the protein binding site such that a two-hybrid complex bound to the binding site can effect transcription of the gene or cDNA comprising the expression cassette.

Methods of producing such a nucleic acid are well known to those of skill in the art and are illustrated in Example 1 herein.

D) The Cells

Virtually any cell can harbor the two-hybrid systems of this invention. Preferred cells, however, are eukaryotic cells and even more preferred cells are mammalian cells and most preferred cells are human cells. The cells can include cells in long term culture (e.g. HeLa cells, CHO cells, SW480 cells, SW48 cells, DLD-1, HCT-116, HT29, 293 cells, U-20S, T-47D, MCF-7, A549, Hep G, Jarkat cells, and the like. The cells can also include acute (unpassaged) cells and cells in vivo.

The cells may be transfected with nucleic acids encoding the chimeric molecules comprising the two-hybrid components of this invention or the chimeric molecules may be directly introduced into the cells (e.g. via microinjection, lipid encapsulation, HIV TAT protein mediated transfer, etc.). In particular, it is noted that the human immunodeficiency virus TAT protein (HIV TAT), when fused to considerably larger proteins results in delivery of the biologically active protein even across the blood brain barrier (see, e.g., Schwarze et al. (1999) *Science*, 285: 1569-1572, and references cited therein).

The cells also preferably include the nucleic acid encoding the protein binding site and an effector molecule according to the methods of this invention.

Depending on the embodiment, the cells may comprise one or more components of the two-hybrid systems of this invention. Thus the cell can include either or both chimeric molecules and/or nucleic acids encoding either or both of the chimeric molecules and/or the nucleic acid comprising the binding site and the effector gene.

III. Placing the Constructs Into a Cell

The chimeric molecules can be introduced directly into the cells, or where the chimeric molecules are fusion proteins, the nucleic acids encoding the proteins can be introduced into the cells according to standard methods known to those of skill in the art.

Where the cells are acute or in culture, standard methods of ex vivo transfection may be utilized. These include, but are not limited to, microinjection, biolistic transfer, lipid-mediated transfer, dendrimer-mediated transfer, electroporation, calcium phosphate transfection, and the like.

Where the chimeric molecules themselves are to be introduced into the cell, standard methods for transferring pharmaceuticals into cells may be used. Such methods include, but are not limited to liposome encapsulation, microinjection, the use of HIV TAT domains to facilitate transfer, and the like.

A) Constructs for Expression of Components of the Two-hybrid System

In order to express the chimeric molecules (e.g. Gal4-β-catenin, Tcf4-VP16, Gal4-Tcf4, β-catenin-VP16, etc.), the gene/cDNA encoding the chimeric molecule is typically placed in an expression cassette. The expression cassette typically comprising regulatory machinery (e.g. eukaryotic promoter, initiation site, stop site, etc.) sufficient to direct expression of the gene and/or cDNA. Using the sequence information provided herein expression cassettes suitable for the expression The gene/cDNA is typically placed under the control of (i.e., operably linked to) a promoter that directs transcription of the subject nucleic acid. The promoter may be constitutive or inducible. Where tissue-specific expression is desired the promoter may be tissue-specific promoter.

A wide variety of tissue-specific promoters may be utilized within the context of the present invention. Representative examples of such promoters include, but are not limited to liver-specific promoters such as phosphoenolpyruvate carboxykinase ("PEPCK") (Hatzogiou et al., (1988) *J. Biol Chem.* 263: 17798-808; Benvenisty et al., (1989) *Proc. Natl. Acad. Sci. USA* 86: 1118-1122; Vaulont et al. (1989) *Mol. Cell. Biol.* 9: 4409-4415); B cell specific promoters such as the IgG promoter; breast carcinoma or hepatocellular carcinoma specific promoters such as Carcinoembryonic Antigen promoter (CEA) (Schrewe et al. (1990) *Mol. and Cell. Biol.* 10: 2738); pancreatic acinar cell specific promoters such as the elastase promoter (Swift et al. (1989) *Genes Develop.* 3: 687-96); breast epithelial specific promoters such as the casein promoter (Doppler et al. (1989) *Proc. Natl. Acad. Sci. USA* 86:104-108); erythoid specific-transcription promoters which are active in erythroid cells, such as the porphobilinogen deaminase promoter (Mignotte et al. (1990) *Proc. Natl. Acad. Sci. USA* 86: 6458-6452); α- or β-globin specific promoters (van Assendelft et al. (1989) *Cell* 56:969-977; Forrester et al. (1989) *Proc. Natl. Acad. Sci. USA* 86: 5439-5443); promoters which regulate skeletal muscle such as the myo-D binding site (Burden (1989) *Nature* 341: 716; Weintraub et al. (1989) *Proc. Natl. Acad. Sci. USA* 86: 5434-5438); promoters which are specific for .beta. cells of the pancrease, such as the insulin promoter (Ohlsson et al. (1988) *Proc. Natl. Acad. Sci. USA* 85: 4228-4231; Karlsson et al. (1989) *Mol. Cell. Biol.* 9: 823-827); promoters which are specific for the pituitary gland, such as the growth hormone factor promoter (Ingraham et al. (1988) *Cell* 55: 519-529; Bodner et al. (1988) *Cell* 55:505-518); promoters which are specific for melanosomes, such as the tyrosine hydroxylase promoter; liver-specific promoters such as the albumin promoter and the alphafetoprotein promoter (Feuerman et al. (1989) *Mol. Cell. Biol.* 9: 4204-4212; Camper and Tilghman (1989) *Genes Develop.* 3: 537-546); breast carcinoma specific promoters such as the HER2/neu promoter (Tal et al. (1987) *Mol. and Cell. Biol.* 7: 2597); liver-specific promoters such as the alcohol dehydrogenase promoter (Felder (1989) *Proc. Natl. Acad. Sci. USA* 86: 5903-5907); T-cell specific promoters such as the T-cell receptor promoter (Anderson et al. (1988) *Proc. Natl. Acad. Sci. USA* 85: 3551-3554; Winoto and Baltimore (1989) *EMBO J.* 8:729-733); bone-specific promoters such as the osteocalcin promoter (Markose et al. (1990) *Proc. Natl. Acad. Sci. USA* 87: 1701-1705; McDonnell et al. (1989) *Mol. Cell. Biol.* 9: 3517-3523; Kerner et al. (1989) *Proc. Natl. Acad. Sci. USA* 86: 4455-4559) the IL-2 promoter, IL-2 receptor promoter, the whey (wap) promoter, and the MHC Class II promoter, and the like.

The constructs may, optionally, include flanking sequences complementary to a region of the host genomic DNA to facilitate integration of the cassette into the host genome (e.g. through homologous recombination as described below). In addition or alternatively, the flanking sequences may optionally comprise one or more recombinase recognition sites (e.g. LoxP or FLP) to facilitate integration of the expression cassette through the use of a recombinase (e.g. Cre).

B) In vivo Transfection

In certain preferred embodiments, the two-hybrid systems of this invention are introduced into cells in vivo to selectively kill cells showing metabolic defects (e.g. certain cancer cells) or to introduce a particular enzymatic activity in a cell where such activity is diminished or lacking. While in some embodiments, the chimeric molecules are introduced into the cells "directly" (e.g. not recombinantly expressed), e.g., using an HIV TAT fusion protein (see, e.g., Schwarze et al. (1999) *Science*, 285: 1569-1572, and references cited therein), in preferred embodiments, the chimeric molecules are recombinantly expressed fusion proteins. Both proteins can be expressed from a single nucleic acid or from separate nucleic acids. Similarly the nucleic acid encoding the protein binding site and the effector cDNA can be a component of the nucleic acid(s) encoding the chimeric molecules or it can be a separate nucleic acid. Typically, the nucleic acid(s) encoding the chimeric molecule(s) and/or the nucleic acid comprising the binding site and the effector are introduced into the cells using standard methods of "gene therapy".

Several approaches for introducing nucleic acids into cells in vivo, ex vivo and in vitro have been used. These include lipid or liposome based gene delivery (WO 96/18372; WO 93/24640; Mannino and Gould-Fogerite (1988) *BioTechniques* 6(7): 682-691; Rose U.S. Pat No. 5,279,833; WO 91/06309; and Felgner et al. (1987) *Proc. Natl. Acad. Sci. USA* 84: 7413-7414) and replication-defective retroviral vectors harboring therapeutic polynucleotide sequence(s) as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808-813; Nabel and Felgner (1993) *TIBTECH* 11: 211-217; Mitani and Caskey (1993) *TIBTECH* 11: 162-166; Mulligan (1993) *Science*, 926-932; Dillon (1993) *TIBTECH* 11: 167-175; Miller (1992) *Nature* 357: 455-460; Van Brunt (1988) *Biotechnology* 6(10): 1149-1154; Vigne (1995) Restorative Neurology and Neuroscience 8: 35-36; Kremer and Perricaudet (1995) *British Medical Bulletin* 51(1) 31-44; Haddada et al. (1995) in *Current Topics in Microbiology and Immunology*, Doerfler and Böhm (eds) Springer-Verlag, Heidelberg Germany; and Yu et al., (1994) *Gene Therapy*, 1: 13-26.

Widely used retroviral vectors include those based upon murine leukemia virus (MuLV), gibbon ape leukemia virus (GaLV), Simian Immunodeficiency virus (SIV), human immunodeficiency virus (HIV), alphavirus, and combinations thereof (see, e.g., Buchscher et al. (1992) *J. Virol.* 66(5) 2731-2739; Johann et al. (1992) *J. Virol.* 66 (5): 1635-1640 (1992); Sommerfelt et al., (1990) *Virol.* 176:58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al. (1994) *Gene Therapy*, supra; U.S. Pat. No. 6,008,535, and the like).

The vectors are optionally pseudotyped to extend the host range of the vector to cells which are not infected by the retrovirus corresponding to the vector. For example, the vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251-3260; Tratschin, et al. (1984) *Mol. Cell. Biol.*, 4: 2072-2081; Hermonat and Muzyczka (1984) *Proc. Natl. Acad. Sci. USA*, 81: 6466-6470; McLaughlin et al. (1988) and Samulski et al. (1989) *J. Virol.*, 63:03822-3828. Cell lines that can be transformed by rAAV include those described in lebkowski et al. (1988) *Mol. Cell. Biol.*, 8:3988-3996. Other suitable viral vectors include herpes virus, lentivirus, and vaccinia virus.

1) Retroviral Transfection Systems

In one particularly preferred embodiment, retroviruses (e.g. lentiviruses) are used to transfect the target cell(s) with nucleic acids encoding the various components to the two-hybrid systems of this invention. Retroviruses, in particular lentiviruses (e.g. HIV, SIV, etc.) are particularly well suited for this application because they are capable of infecting a non-dividing cell. Methods of using retroviruses for nucleic acid transfection are known to those of skill in the art (see, e.g., U.S. Pat. No. 6,013,576).

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. In preferred embodiments, a helper virus need not be utilized for the production of the recombinant retrovirus since the sequences for encapsidation can be provided by co-transfection with appropriate vectors.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins.

In one preferred embodiment, the invention provides a recombinant retrovirus capable of infecting a non-dividing cell. The recombinant retrovirus comprises a viral GAG, a viral POL, a viral ENV, a heterologous nucleic acid sequence operably linked to a regulatory nucleic acid sequence, and cis-acting nucleic acid sequences necessary for packaging, reverse transcription and integration, as described above. It should be understood that the recombinant retrovirus of the invention is capable of infecting dividing cells as well as non-dividing cells.

In preferred embodiments, the recombinant retrovirus is therefore genetically modified in such a way that some of the structural, infectious genes of the native virus (e.g. env, gag, pol) have been removed and replaced instead with a nucleic acid sequence to be delivered to a target non-dividing cell (e.g., a sequence encoding various components of the two-hybrid systems of this invention). After infection of a cell by the virus, the virus injects its nucleic acid into the cell and the retrovirus genetic material may on occasion integrate into the host cell genome. Whether integrated or episomal, the transferred retrovirus genetic material is then transcribed and translated into the various components of the two-hybrid system of this invention within the host cell. Methods of making and using lentiviral vectors are discussed in detail in U.S. Pat. Nos. 6,013,516, 5,932,467, and the like.

2) Adenoviral Vector Systems

In another preferred embodiment, one or more components of the two-hybrid systems of this invention are expressed in an adenoviral vector suitable for gene therapy. The use of adenoviral vectors is described in detail in WO 96/25507. Particularly preferred adenoviral vectors are described by Wills et al. (1994) *Hum. Gene Therap.* 5: 1079-1088. Typically, adenoviral vectors contain a deletion in the adenovirus early region 3 and/or early region 4 and this deletion may include a deletion of some or all of the protein IX gene. In one embodiment, the adenoviral vectors include deletions of the E1a and/or E1b sequences.

A number of different adenoviral vectors have been optimized for gene transfer. One such adenoviral vector is described in U.S. Pat. No. 6,020,191. This vector comprises a CMV promoter to which a transgene may be operably linked and further contains an E1 deletion and a partial deletion of 1.6 kb from the E3 region. This is a replication defective vector containing a deletion in the E1 region into which a transgene (e.g. the β subunit gene) and its expression control sequences can be inserted, preferably the CMV promoter contained in this vector. It further contains the wild-type adenovirus E2 and E4 regions. The vector contains a deletion in the E3 region which encompasses 1549 nucleotides from adenovirus nucleotides 29292 to 30840 (Roberts et al. (1986) *Adenovirus DNA, in Developments in Molecular Virology*, W. Doerfler, ed., 8: 1-51). These modifications to the E3 region in the vector result in the following: (a) all the downstream splice acceptor sites in the E3 region are deleted and only mRNA a would be synthesized from the E3 promoter (Tollefson et al. (1996) *J, Virol.* 70:2 296-2306, 1996; Tollefson et al. (1996) Virology 220: 152-162,); (b) the E3A poly A site has been deleted, but the E3B poly A site has been retained; (c) the E3 gp19K (MHC I binding protein) gene has been retained; and (d) the E3 11.6K (Ad death protein) gene has been deleted.

Such adenoviral vectors can utilize adenovirus genomic sequences from any adenovirus serotypes, including but not limited to, adenovirus serotypes 2, 5, and all other preferably non-oncogenic serotypes.

In one preferred embodiment, the cytomegalovirus (CMV) immediate early promoter (Boshart et al. (1985) Cell 41: 521-530) is used to control expression of the chimeric molecules comprising the two-hybrid systems of this invention. The CMV promoter is positioned 5' to the transgene(s) in a transcription unit. Portions of the full-length promoter can be tested for their ability to allow persistent expression of the transgene.

Polyadenylation signals which may be positioned at the 3' end of the transgene in include, but are not limited to, those derived from bovine growth hormone (BGH) and SV40.

In one embodiment, to create the recombinant adenoviral vectors of the invention which contain a transcription unit (expression cassette) encoding a component of the two-hybrid systems described herein, a plasmid containing the transcription unit inserted into an adenovirus genomic fragment is co-transfected with a linearized viral genome derived from an adenoviral vector of interest into a recipient cell under conditions whereby homologous recombination occurs between the genomic fragment and the virus. Preferably, the transcription unit is engineered into the site of an E1 deletion. As a result, the transcription unit encoding a desired transgene is inserted into the adenoviral genome at the site in which it was cloned into the plasmid, creating a recombinant adenoviral vector. Following the homologous recombination, the vector genome is encapsidated into virions as evidenced by the formation of viral plaques. Preparation of replication-defective vector stocks can be accomplished using cell lines that complement viral genes deleted from the vector, e.g., 293 or A549 cells containing the deleted adenovirus E1 genomic sequences. After amplification of plaques in suitable complementing cell lines, the viruses can be recovered by freeze-thawing and subsequently purified using cesium chloride centrifugation. Alternatively, virus purification can be performed using chromatographic techniques (e.g., as set forth in International Application No. PCT/US96/13872.

Titers of replication-defective adenoviral vector stocks can be determined by plaque formation in a complementing cell line, e.g., 293 cells. For example, end-point dilution using an antibody to the adenoviral hexon protein may be used to quantitate virus production (Armentano et al. (195) *Hum. Gene Ther.* 6:1343-1353).

3) Non-viral Transfection

Alone, or in combination with viral vectors, a number of non-viral vectors are also useful for transfecting cells with the nucleic acid constructs described herein. Suitable non-viral vectors include, but are not limited to, plasmids, cosmids, phagemids, liposomes, water-oil emulsions, polethylene imines, biolistic pellets/beads, and dendrimers.

Liposomes were first described in 1965 as a model of cellular membranes and quickly were applied to the delivery of substances to cells. Liposomes entrap DNA by one of two mechanisms which has resulted in their classification as either cationic liposomes or pH-sensitive liposomes. Cationic liposomes are positively charged liposomes which interact with the negatively charged DNA molecules to form a stable complex. Cationic liposomes typically consist of a positively charged lipid and a co-lipid. Commonly used co-lipids include dioleoyl phosphatidylethanolamine (DOPE) or dioleoyl phosphatidylcholine (DOPC). Co-lipids, also called helper lipids, are in most cases required for stabilization of liposome complex. A variety of positively charged lipid formulations are commercially available and many other are under development. Two of the most frequently cited cationic lipids are lipofectamine and lipofectin. Lipofectin is a commercially available cationic lipid first reported by Phil Felgner in 1987 to deliver genes to cells in culture. Lipofectin is a mixture of N-[1-(2,3-dioleyloyx)propyl]-N-N-N-trimethyl ammonia chloride (DOTMA) and DOPE.

DNA and lipofectin or lipofectamine interact spontaneously to form complexes that have a 100% loading efficiency. In other words, essentially all of the DNA is complexed with the lipid, provided enough lipid is available. It is assumed that the negative charge of the DNA molecule interacts with the positively charged groups of the DOTMA. The lipid:DNA ratio and overall lipid concentrations used in forming these complexes are extremely important for efficient gene transfer and vary with application. Lipofectin has been used to deliver linear DNA, plasmid DNA, and RNA to a variety of cells in culture. Shortly after its introduction, it was shown that lipofectin could be used to deliver genes in vivo. Following intravenous administration of lipofectin-DNA complexes, both the lung and liver showed marked affinity for uptake of these complexes and transgene expression. Injection of these complexes into other tissues has had varying results and, for the most part, are much less efficient than lipofectin-mediated gene transfer into either the lung or the liver.

PH-sensitive, or negatively-charged liposomes, entrap DNA rather than complex with it. Since both the DNA and the lipid are similarly charged, repulsion rather than complex formation occurs. Yet, some DNA does manage to get entrapped within the aqueous interior of these liposomes. In some cases, these liposomes are destabilized by low pH and hence the term pH-sensitive. To date, cationic liposomes have been much more efficient at gene delivery both in vivo and in vitro than pH-sensitive liposomes. pH-sensitive liposomes have the potential to be much more efficient at in vivo DNA delivery than their cationic counterparts and should be able to do so with reduced toxicity and interference from serum protein.

In another approach dendrimers complexed to the DNA have been used to transfect cells. Such dendrimers include, but are not limited to, "starburst" dendrimers and various dendrimer polycations.

Dendrimer polycations are three dimensional, highly ordered oligomeric and/or polymeric compounds typically formed on a core molecule or designated initiator by reiterative reaction sequences adding the oligomers and/or polymers and providing an outer surface that is positively changed. These dendrimers may be prepared as disclosed in PCT/US83/02052, and U.S. Pat. Nos. 4,507,466, 4,558,120, 4,568,737, 4,587,329, 4,631,337, 4,694,064, 4,713,975, 4,737,550, 4,871,779, 4,857,599.

Typically, the dendrimer polycations comprise a core molecule upon which polymers are added. The polymers may be oligomers or polymers which comprise terminal groups capable of acquiring a positive charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl, and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Oligomers and polymers suitable for the preparation of the dendrimer polycations of the invention are pharmaceutically-acceptable oligomers and/or polymers that are well accepted in the body. Examples of these are polyamidoamines derived from the reaction of an alkyl ester of an $\alpha,\beta$-ethylenically unsaturated carboxylic acid or an $\alpha,\beta$-ethylenically unsaturated amide and an alkylene polyamine or a polyalkylene polyamine, among others. Preferred are methyl acrylate and ethylenediamine. The polymer is preferably covalently bound to the core molecule.

The terminal groups that may be attached to the oligomers and/or polymers should be capable of acquiring a positive charge. Examples of these are azoles and primary, secondary, tertiary and quaternary aliphatic and aromatic amines and azoles, which may be substituted with S or O, guanidinium, and combinations thereof. The terminal cationic groups are preferably attached in a covalent manner to the oligomers and/or polymers. Preferred terminal cationic groups are amines and guanidinium. However, others may also be utilized. The terminal cationic groups may be present in a proportion of about 10 to 100% of all terminal groups of the oligomer and/or polymer, and more preferably about 50 to 100%.

The dendrimer polycation may also comprise 0 to about 90% terminal reactive residues other than the cationic groups. Suitable terminal reactive residues other than the terminal cationic groups are hydroxyl, cyano, carboxyl, sulfhydryl, amide and thioether, among others, and combinations thereof. However others may also be utilized.

The dendrimer polycation is generally and preferably non-covalently associated with the polynucleotide. This permits an easy disassociation or disassembling of the composition once it is delivered into the cell. Typical dendrimer polycation suitable for use herein have a molecular weight ranging from about 2,000 to 1,000,000 Da, and more preferably about 5,000 to 500,000 Da. However, other molecule weights are also suitable. Preferred dendrimer polycations have a hydrodynamic radius of about 11 to 60 Å., and more preferably about 15 to 55 Å. Other sizes, however, are also suitable. Methods for the preparation and use of dendrimers in gene therapy are well known to those of skill in the art and describe in detail, for example, in U.S. Pat. No. 5,661,025

Where appropriate, two or more types of vectors can be used together. For example, a plasmid vector may be used in conjunction with liposomes. In the case of non-viral vectors, nucleic acid may be incorporated into the non-viral vectors by any suitable means known in the art. For plasmids, this typically involves ligating the construct into a suitable restriction site. For vectors such as liposomes, water-oil emulsions, polyethylene amines and dendrimers, the vector and construct may be associated by mixing under suitable conditions known in the art.

D) Ex vivo Gene Therapy

The methods of this invention are not restricted to the treatment of cells in vivo. Thus, in certain embodiments, this invention contemplate ex vivo transfection of cells with two-hybrid systems designed to supplement a particular enzymatic activity where such is lacking.

Ex vivo cell transformation for diagnostics, research, or for gene therapy (e.g., via re-infusion of the transformed cells into the host organism) is well known to those of skill in the art. In a preferred embodiment, cells are isolated from the subject organism, transfected with the constructs of this invention and, optionally, re-infused back into the subject organism (e.g., patient).

VI. Kits

In still another embodiment, this invention provides kits for practice of the methods described herein. In certain embodiments the kits comprise a nucleic acid encoding one or both of the chimeric molecules used in the two-hybrid systems of this invention. Thus, for example, in the case of the APC two-hybrid system described in example 1, the kit may comprise a nucleic acid encoding a Gal4-β-catenin, and/or a Tcf-VP16, and/or a Gal4-Tcf, and/or a β-catenin-VP16. Certain kits may comprise the chimeric molecules themselves (e.g. the fusion proteins). The kits may alternatively or additionally include a nucleic acid encoding a polypeptide binding site and an effector gene. The nucleic acids may be provided as components of vectors (e.g. flanked by appropriate restriction sites and/or PCR primer binding sites). The nucleic acid constructs encoding the chimeric molecules may contain the "fusion gene" under the control of a constitutive, an inducible, or a tissue specific promoter. Such promoters are well known to those of skill in the art.

In certain embodiments, the kits comprise a cell (e.g. a mammalian cell, more preferably a human cell) comprising one or more of the components of a two-hybrid system as described herein.

The kits may optionally include any reagents and/or apparatus to facilitate practice of the methods described herein. Such reagents include, but are not limited to buffers, instrumentation (e.g. bandpass filter), reagents for detecting a signal from a reporter gene, transfection reagents, cell lines, vectors, and the like.

In addition, the kits may include instructional materials containing directions (i.e., protocols) for the practice of the methods of this invention. Preferred instructional materials provide protocols utilizing the kit contents for screening for modulators of a cells ability to accumulate or to degrade a metabolic product, and/or for methods of selectively killing a cell that is has an abnormal metabolic pathway, and/or for methods of selectively expressing an enzymatic activity to supplement a cell having said activity diminished or non-existant as described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Applied Use of Mammalian Two-hybrid System for APC-mutated Colon Cancer Therapeutics Accumulation of β-catenin in cytoplasm is one of the crucial events found in adenomatous polyposis coli (APC) gene-mutated colon cancer cells. The mutated APC gene produces truncated form of APC protein that lacks the affinity to β-catenin protein. The accumulation of β-catenin protein is caused by β-catenin avoiding from degradation mechanisms via the ubiquitin-proteasome pathway, which requires phosphorylation of β-catenin/APC complex by glycogen synthase kinase 3β (GSK-3β). In this example, we describe a novel gene-therapy system that selectively kills APC mutated-cell. This system is made of mammalian two-hybrid system that consists of GAL4/β-catenin, VP16/Tcf4 and the suicide gene generated output gene DNA construct. This system is designed to works only when accumulation of GAL4/β-catenin occurs. In APC-mutated human colon cancer cell line SW480, accumulation of GAL4/β-catenin in the presence of VP16/TCF4 proteins caused a high expression level of the output gene. In contrast, in other human cell lines that have APC wild type such as SW48, degradation of GAL4/β-catenin was observed and expression levels of the output gene was kept low. Addition of the wild type APC expression plasmid with the two-hybrid constructs in SW480 cells resulted in the reduction of the output gene expression levels as well as the reduction of GAL4/and intact β-catenin levels. Replacement of the output gene from the reporter gene to the suicide gene made this two-hybrid system possible to kill SW480 cells. We exchanged the firefly luciferase cDNA of the pG5 plasmid to the p53-EGFP cDNA, and transfected to SW480 cells in the presence of other two-hybrid components. About 80% of EGFP-positive cells were dead in the p53-EGFP transfected cells, while only 20% of EGFP-positive cells were dead in the control EGFP transfected cells. We believe this system is applicable for broader uses in gene therapy targeting diseases that involve protein degradation disorders.

Introduction

Mutation of the adenomatous polyposis coli (APC) tumor suppressor gene, which was found in Familial Adenomatous Polyposis (FAP) patients (Kinzler et al. (1991) *Science*, 253: 661-665; Nishisho et al. (1991) *Science*, 253: 665-669), had also frequently been found in sporadic colorectal cancer patients (Sparks et al. (1998) *Cancer Res.*, 58: 1130-1134). Functional studies of APC revealed that wild type APC protein provides an optimal environment for glycogen synthase kinase-3β (GSK-3β) to phosphorylate β-catenin, which was originally found as a component of cell adhesion molecules (Rubinfeld et al. (1996) *Science*, 272: 1023-1026, and accelerates the degradation of cytoplasmic β-catenin via the ubiquitin-proteasome pathway (Aberle et al. (1997) *EMBO J.*, 16: 3797-3804; Winston et al. (1999) *Genes Dev.*, 13: 270-283). The functional loss of APC by genetic mutation in colorectal cancer hence causes the accumulation of β-catenin (Munemitsu et al. (1995) *Proc. Natl. Acad. Sci., USA*, 92: 3046-3050). The fact that around 80% of colorectal cancer cells have dysfunctional APC (Sparks et al. (1998) *Cancer Res.*, 58: 1130-1134) and that others have some mutations in the GSK-3β phosphorylation site of β-catenin, which also stabilizes β-catenin protein in the cells (Munemitsu et al. (1996) *Mol. Cell. Biol.*, 16: 4088-4094), implies accumulation of β-catenin in cytoplasm is one of the crucial events for colorectal cancer formation. Moreover, in the gene manipulated mice model, both APC-mutated mice (Shibata et al. (1997) *Science*, 278: 120-123) and β-catenin-mutated mice (Harada (1999) *EMBO J.*, 18: 5931-5942) formed intestinal polyps. These mutations are observed at the early stage of colon cancer development even before ras or p53 mutation (Laurent-Puig et al. (1999) *Eur. J. Cancer Prev.*, 8: Suppl 1 S39-47). Recent studies have reported that accumulated β-catenin in colorectal cancer forms complex with transcription factor T cell factor 4 (Tcf4) (Korinek et al. (1997) *Science*, 275: 1784-1787; Morin et al. (1997) *Science*, 275: 1787-1790) and intensifies the Tcf/lef-1-dependent oncogenic genes expression such as cyclin D1 (Tetsu and McCormick (1999) *Nature*, 398: 422-426, c-myc (He et al. (1998) *Science*, 281: 1509-1512) and peroxisome proliferator-activated receptor δ (He et al. (1999) *Cell*, 99: 335-345).

The yeast two-hybrid system has been used as one of the most convenient tools to study protein-protein interactions or to identify the interacting partners for certain proteins (Dang et al. (1991) *Mol. Cell. Biol.*, 11: 954-962). This system consists of basically three components. The first component is the fusion protein that contains the DNA binding domain of a transcription factor. The second component is the fusion protein that contains the transcription activation domain of a transcription factor. The third component is the output gene expression construct that has the consensus sequence for the first component and is followed by the transcription activation site, such as TATA box, for the second component. As the first component, the yeast GAL4 DNA binding domain is widely used, and as the second component, the herpes simplex virus VP16 transcription activation domain is widely used. A few years after this yeast two-hybrid system was developed, it was modified for mammalian cells by replacing promoter regions of the fusion protein expression plasmids (Fearon et al. (1992) *Proc. Natl. Acad. Sci., USA*, 89: 7958-7962). This modification made it possible to study the functional binding of two proteins in mammalian cells by measuring the output gene expression. In this paper, we introduce a unique application of the mammalian two-hybrid system. We used β-catenin and Tcf4 as binding modules for two-hybrid system with the combination of the cell death inducing gene output, and performed a selective cell killing study using APC mutant cells (FIG. 1).

Materials and Methods

Cells

All the human cancer cell lines used here were obtained from the American Type Culture Collection (Rockville, Md.). Human colon cancer cell lines SW480 and SW48 were maintained in Leivovitz's L-15 medium (Life Technologies Inc., Gaithersburg, Md.) supplemented with 10% heat-inactivated FBS (Life Technologies Inc.) in a 0.8% $CO_2$ incubator at 37° C. The human osteosarcoma cell line U2-OS and embryonic kidney cell line 293 were maintained in RPMI1640 medium (Life Technologies Inc) supplemented with 10% FBS in a 5% $CO_2$ incubator at 37° C.

Plasmids

The pBIND, pBIND/Id, pACT and pG5Luc plasmids were purchased from Promega (Madison, Wis.). The pp53-EGFP was purchased from Clontech (Palo Alto, Calif.). The GAL4 fusion β-catenin expression plasmid, pBIND/β-catenin, and VP16 fusion Tcf4 expression plasmids, pACT/Tcf4, were prepared as followed. The human β-catenin cDNA with Bam HI linker was prepared with PCR and cloned into Bam HI site of pBIND. The human Tcf4 cDNA with Bam HI linker was prepared with PCR and cloned into Bam HI site of pACT. The pcDNA3/p53-EGFP was prepared by generating Kpn I and Xba I fragment of the pp53-EGFP, into Kpn I/Xba I site of pcDNA3.1 (Invitrogen, Carlsbad, Calif.). The pG5/p53-EGFP plasmid was constructed by inserting the p53-EGFP cDNA fragment of pp53-EGFP to Bgl II and Hind III site of pG5Luc. The pG5/EGFP plasmid was constructed by deleting p53 cDNA from the pG5/p53-EGFP plasmid. The p53-Luc, pAP-1-Luc and pCRE-Luc plasmids were purchased from Stratagene (La Jolla, Calif.).

Immunostaining

Cells grown to 50-80% confluency were trypsinized and washed twice with phosphate buffer saline (PBS), and lysed in TE buffer (10 mM Tris, 1 mM EDTA) containing protease inhibitors (Complete Mini™, Boehringer Mannheim). Cell lysate samples were separated with 4-20% acrylamide linear gradient SDS-PAGE gel (Bio-Rad, Cambridge, Mass.), transferred onto nitrocellulose membrane, incubated with primary antibodies, horseradish peroxydase-conjugated secondary antibodies, and detected with Enhanced Chemiluminescence (ECL) kit (Amersham Pharmacia Biotech, Uppsala, Sweden). Anti β-catenin (sc-7199), GAL4 (sc-577), VP16 (sc-7546), p53 (sc-126) antibodies were purchased from Santa Cruz Biotechnology (Santa Cruz, Calif.). Anti-APC (OP44) antibody was from Calbiochem Novabiochem (Sandiego, Calif.). Anti-Tcf4 antibody was obtained from Upstate Biotechnology Inc. (Lake Placid, N.Y.). Horseradish-conjugated anti-mouse or anti rabbit IgG antibodies were from Amersham Pharmacia Biotech.

Two-hybrid Assay

The pBIND/β-catenin, pACT/Tcf4 and pG5/luc plasmids were co-transfected to cells using TransFast™ (Promega) according to the manufacturer's recommended protocol. Briefly, cells were seeded in 24-well plates at a density of $5 \times 10^4$ cells/well and cultured for 24 h. Total 1 μg/well of plasmids were transfected and cultured for another 24 h. Finally, luciferase activity was measured with a commercially available kit (Promega). The transfection efficiency was normalized by renilla luciferase activity, which was simultaneously expressed from the pBIND plasmids.

FACS Analysis

The pG5/p53-EGFP or pG5/EGFP plasmid was co-transfected with pBIND/WT-β-catenin and pACT/FL-Tcf4 plasmids to SW480 cells. After 48-72 h incubation, cells were trypsinized and washed twice with PBS. Cells were suspended in PBS containing 10 μM propydium iodide, and analyzed on a FACScan flow cytometer (Becton Dickinson, San Jose, Calif.). Cell viability profile of EGFP-positive cells were analyzed by the uptake of propydium Iodide.

Results

Functional Expression of Two-hybrid Proteins in Colon Cancer Cell Line.

Figure 2A:
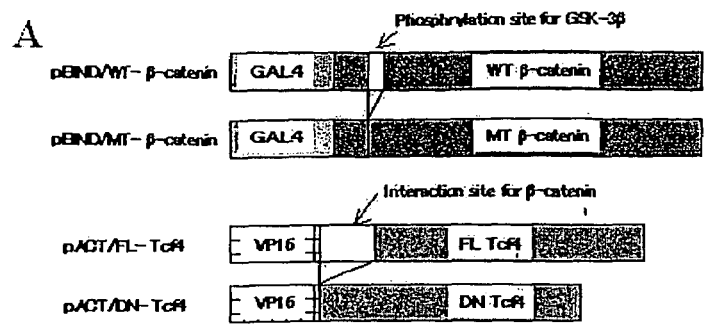
FIG. 2A FIG. 2B, and FIG. 2C illustrate the two-hybrid system of this invention.
Figure 2B:
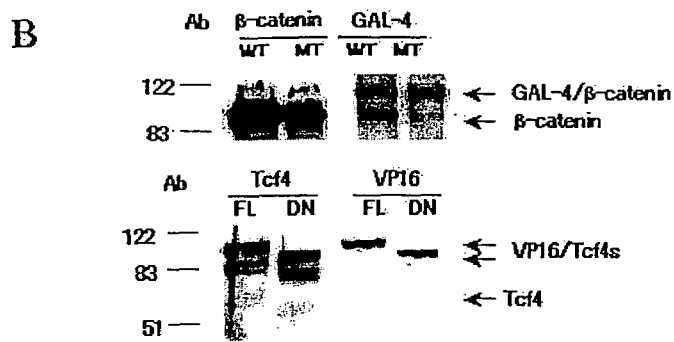
Figure 2C:
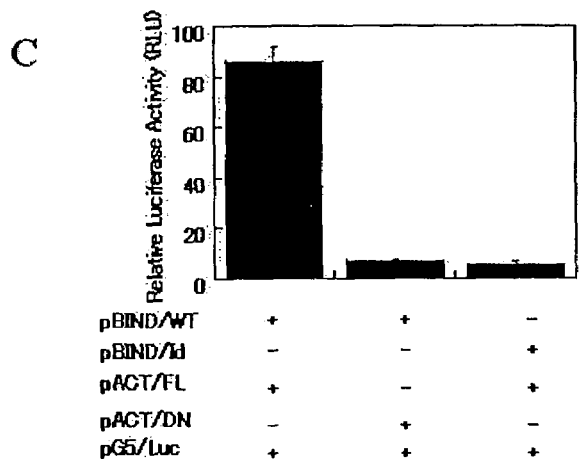

We constructed four fusion protein expression-plasmids, pBIND/WT-β-catenin, pBIND/MT-β-catenin, pACT/FL-Tcf4 and pACT/DN-Tcf4, which express GAL4/WT-β-catenin, GAL4/MT-β-catenin, VP16/FL-Tcf4 and VP16/DN-Tcf4 respectively (FIG. 2A). GAL4/WT-β-catenin is a fusion protein that consists of the DNA binding domain of yeast GAL4 protein and full length human β-catenin. GAL4/MT-β-catenin has a truncated form of β-catenin, which lacks GSK-3β recognition site. VP16/FL-Tcf4 is a fusion protein which consists of the transcription activation domain of herpes simplex virus VP16 and full length human Tcf4. VP16/DN-Tcf4 has a truncated form of Tcf4, which lacks the β-catenin binding site. We transfected pBIND/WT-β-catenin, pBIND/MT-β-catenin, pACT/FL-Tcf4 or pACT/DN-Tcf4 to SW480 cells and detected those fusion protein expression levels using immunoblotting. Expressed GAL4/β-catenin fusion proteins were recognized by both anti-GAL4 and anti-β-catenin antibodies, as well as VP16/Tcf4 proteins, which were recognized by both anti-VP16 and anti-Tcf4 antibodies (FIG. 2B). The co-transfection of pBIND/WT-β-catenin, pACT/FL-Tcf4 and pG5/Luc led to an expression of the output gene, firefly luciferase, (FIG. 2C). This output gene expression level was strictly controlled by the expression of the GAL4/β-catenin and VP16/FL-Tcf4 combination, as the replacement of pBIND/WT-β- catenin plasmid to pBIND/Id or pACT/FL-Tcf4 plasmid to pACT/DN-Tcf4 failed to raise the firefly luciferase activity.

Regulation of β-Catenin/Tcf4 Two-hybrid System by APC.

Figure 3A:
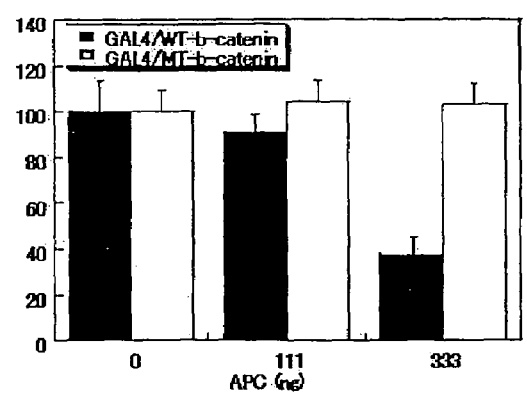
FIG. 3A and FIG. 3B illustrate APC dependent selective expression and detecton of two-hybrid component proteins in SW48 cells.
Figure 3B:
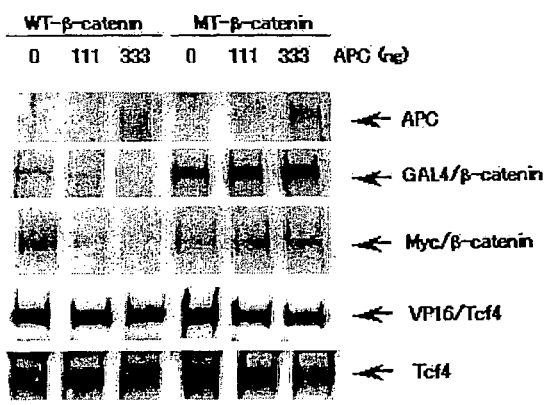

As those fusion proteins properly manipulate the output gene expression levels, we next examined whether the GAL4/WT-β-catenin protein was degradable, as well as intact wild type β-catenin protein, dependent on the APC profile. First, co-transfection of the wild type APC expression plasmid with pBIND/WT or MT-β-catenin, pACT/FL-Tcf4, and pG5/Luc in SW480 cells was examined. Addition of APC in the pBIND/WT-β-catenin system resulted in a drastic decrease of firefly luciferase activity, whereas pBIND/MT-β-catenin system was not affected by APC expression (FIG. 3A). Next, the protein levels of GAL4/β-catenin and VP16/Tcf4 were detected in the same condition as reporter gene assay. As a positive control experiment, the pcDNA3/myc-β-catenin was co-transfected with the pcDNA/APC plasmid. In the presence of APC protein, both GAL4/WT-β-catenin and myc-tagged WT-β-catenin protein levels were reduced, whereas neither GAL4/MT-β-catenin nor myc-tagged MT-β-catenin protein levels were changed (FIG. 3B). Neither VP16/Tcf4 nor intact Tcf4 protein levels were affected by APC expression.

Regulation of β-Catenin/Tcf4 Two-hybrid System in Various Cell Types.

Figure 4A:
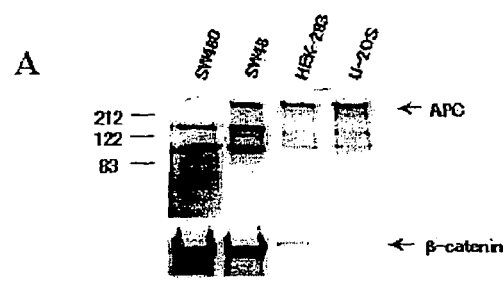
FIG. 4A, FIG. 4B, and FIG. 4C illustrate expression of cytoplasmic β-catenin, detection of Gal4 fusion protein degradation products, and selective gene expression dependent on the APC profile of the target cell.
Figure 4B:
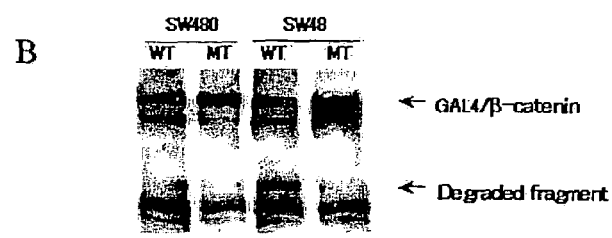
Figure 4C:
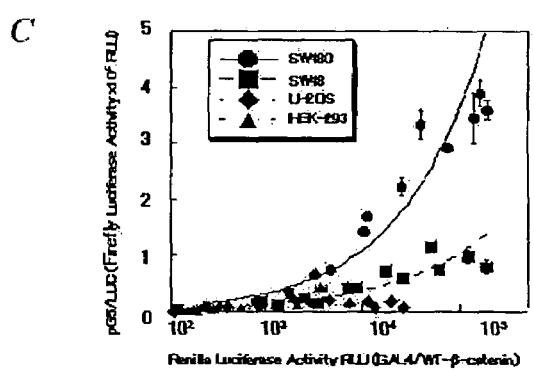

In order to confirm these results, we performed the two-hybrid assay using human osteosarcoma U-20S and human embryonic kidney 293 cells, which were suppose to express wild type APC. We examined the expression levels of cytoplasmic β-catenin and APC first (FIG. 4A). Both U-20S and 293 showed low levels of cytoplasmic β-catenin. These two cell lines also showed an APC band at the expected molecular size. These results indicated that the degradation mechanism of β-catenin worked properly in these cell lines. SW480, which is known as an APC mutated cell line, did not show an APC band at the expected size. SW48, which is known as a β-catenin mutated-cell line, exhibited high levels of β-catenin despite of having wild type APC. FIG. 4B shows the expression levels of GAL4/WT or MT-β-catenin proteins in SW480 cells and SW48 cells. There was a specific lower band observed only in SW48 cells that expressed GAL4/WT-β-catenin which implied GAL4/WT-β-catenin but not GAL4/MT-β-catenin was degraded in APC wild type cell line. All of the cell lines examined that have wild type APC showed lower output gene expression levels than SW480 cells (FIG. 4C). Moreover, SW48 cells showed similar amount of the output gene expression levels to SW480 cells, when transfected with the two-hybrid system using GAL4/MT-β-catenin (data not shown). These results implied that APC profile of the cells was a very important factor to control the output gene expression levels.

Application of Mammalian Two-hybrid System to in vitro Gene Therapy.

Figure 5A:
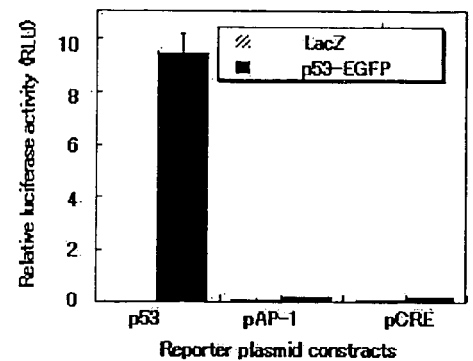
FIG. 5A, FIG. 5B, and FIG. 5C illustrate activation of p53 responsive luciferase expression and detection of p53-EGFP.
Figure 5B:
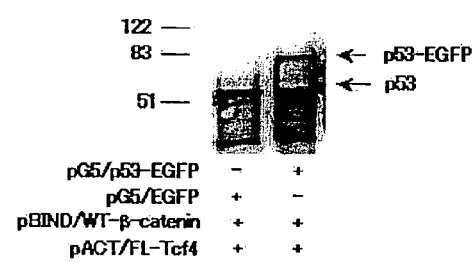
Figure 5C:
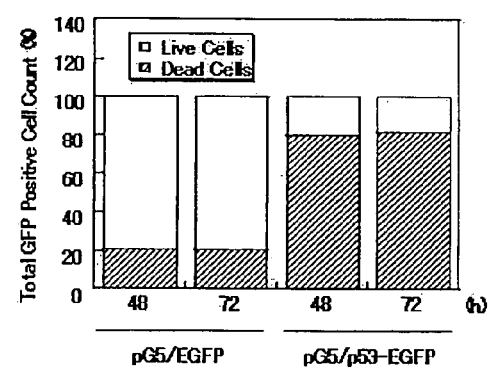

As we figured out that this two-hybrid system selectively worked under dysfunctional APC existing environment, we decided to replace the output gene from luciferase to p53-EGFP. First we expressed p53-EGFP in SW480 cells in the presence of p53 responsive element-driven luciferase plasmid to examine whether the p53-EGFP fusion protein was functionally the same as wild type p53. Transfected p53-EGFP selectively activated the p53 responsive element-driven luciferase, while negative control lacZ did not activate p53 responsive element-driven luciferase (FIG. 5A). The p53-EGFP expression was observed as green light under the fluorescent microscope (data not shown), and also recognized as 80 kDa protein by anti-p53 antibody (FIG. 5B). The viability of those p53-EGFP expressing cells was analyzed by flowcytometory using the propydium iodide incorporation method. The two-hybrid plasmids-transfected cells were harvested after 48 h or 72 h incubation. About 20% of the pG5/p53-EGFP plasmid-transfected cells survived, while about 80% of the pG5/EGFP-transfected cells survived (FIG. 5C). In this experiment, pG5/EGFP transfected cells showed a higher intensity of GFP light than pG5/p53-EGFP transfected cells (data not shown). Probably, p53-EGFP expressing cells started dying before the expression levels of p53-EGFP reached those as high as EGFP.

Discussion

Gene therapy as an approach for cancer therapy is relatively new. Previously, inefficient or non-specific delivery methods have proven problematic for such approaches (Verma and Somia (1997) *Nature*, 389: 239-242). In order to compensate for insufficient delivery efficiency, unique specified selectivity toward cancer cells is desired. For instance, tissue specific promoter-driven suicide gene expression is one of the ideas to prevent damage to non-cancer cells (Vandier et al. (1988) *Cancer Res.*, 58: 4577-4580)

In this paper, we suggest two novel concepts that can improve the selectivity of gene therapy. One is to target the cancer cell-specific protein-degradation disorder, and the other is to use the mammalian two-hybrid system to control suicide gene expression. Accumulation of β-catenin in cytoplasm occurs in most of the colon cancer cells, and about 80% of those are caused by dysfunctional APC (Kinzler and Vogelstein (1996) *Cell*, 87: 159-170). Our system takes advantage of the fact that β-catenin is not degraded quickly in APC-mutated cells. Even as a GAL4 fusion protein, GAL4/WT-β-catepin protein was scavenged via the APC-dependent degradation pathway (FIG. 3B). The important fact in this event is that the β-catenin in this system should not necessarily be a full-length wild type protein, as far as it can activate output gene expression and can be degradable via the APC-dependent pathway. The minimum component of the β-catenin protein for this two-hybrid system is the phosphorylation site for GSK-3β, binding domain for APC and Tcf4. The C terminus part, after the last armadillo domain of β-catenin, might not be necessary as this part is considered to have a transcription activation function. It will also make the system more efficient if the affinity of GAL4/WT-β-catein can be preferable to APC but not to E-cadherin by deleting or mutating some part of armadillo structure. As far as the VP16/Tcf4, the N terminus β-catenin binding domain is the only necessary domain from Tcf4 protein for the two-hybrid system. This truncation of DNA binding domain may reduce the possibility of unnecessary gene expression by VP16/Tcf4 recognizing Tcf consensus sequence in the nuclei. At least, co-transfection of pACT/FL-Tcf4 and Top Flash (Korinek et al. (1997) *Science*, 275: 1784-1787) plasmids did not induce any significant Tcf consensus sequence based gene transactivation (data not shown). Another possible event that may occur is that over-expression of VP16/Tcf4 does not cause unwanted gene activation because the Tcf4 on the DNA without β-catenin forms a complex with groucho (Roose et al. (1998) Nature, 395: 608-612) and would rather work as a target gene suppressor than gene transcription activator. Additionally, it is possible to improve the selectivity of this therapy method for colon cancer cells by using a promoter that has a functional Tcf4 responsive element for the expression of GAL4 fusion protein and VP16 fusion protein, so that the expression levels of those proteins would be selectively higher in colon cancer cells. The cyclin D1 (Tetsu and McCormick (1999) *Nature*, 398: 422-426) or c-myc (He et al. (1998) *Science*, 281: 1509-1512) promoters may be good candidates for this purpose.

As a safer protocol, instead of introducing all components at one time, the VP16/FL-Tcf4 and pG5/p53-EGFP constructs should be introduced first with some marker expression plasmid such as blue fluorescence protein (BFP) using methods such as infectious RNA with GeneGun (Mandl et al. (1998) *Nat Med.*, 4: 1438-1440) or adenovirus delivery system to obtain enough expression levels of VP16/FL-Tcf4. After confirming expression levels of the first sets of genes, GAL4/WT-β-catenin should be introduced by using the method that you can manipulate the expression levels of out put gene, i.e. using Tcf4 responsive element-driven promoter. In order to perform quicker expression of GAL4-β-catenin protein than gene delivery, using TAT-tag fusion protein also seems to be a fascinating option (Nagahara et al. (1998) *Nat Med.*, 4: 1449-1452). It is a very important advantage of the two-hybrid system for gene therapy that the expression level of the output gene is manageable by the amount of GAL4/WT-β-catenin to prevent the side effect on patients. And as far as the expression levels of output gene is tightly regulated, the choice for the output genes can be broader, i.e. p53, Bax, herpes simplex virus thymidine kinase (HSV-TK), caspases, and so on.

From a broader point of view, this system may be applicable to other diseases than colon cancer, as far as the diseases involve a protein degradation disorder and the abnormally accumulated protein has an interacting partner. Moreover, if the two-hybrid part may work as a bio-sensor for a specific signal transduction and detect the event in vivo, i.e. increase of blood glucose concentration, the gene which modulates the event can be chosen as an output gene, i.e. insulin or insulin receptor for diabetes patients.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cell comprising:
   an accumulation or degradation of a metabolic product;
   a nucleic acid encoding a peptide binding site and an effector gene;
   a first chimeric protein comprising a nucleic acid binding protein that binds said peptide binding site where said nucleic acid binding protein is attached to said metabolic product or to a ligand that binds to said metabolic product; and
   a second chimeric protein comprising an expression control protein attached to said metabolic product or to said ligand that binds to said metabolic product such that when said first chimeric protein comprises said metabolic product, said second chimeric protein comprises said ligand and when said first chimeric protein comprises said ligand, said second chimeric protein comprises said metabolic product;
   wherein said cell is a cell selected from the group consisting of SW480, SW48, DLD-1, HCT-116, HT29, 293, U-20S, T-47D, MCF-7, HeLa, A549, Hep G2, a mammalian cell, and a Jarkat cell.

2. The cell of claim 1, wherein said expression control protein is a transactivator.

3. The cell of claim 2, wherein said transactivator is VP16.

4. A cell comprising:
   an accumulation or degradation of a metabolic product;
   a nucleic acid encoding a peptide binding site and an effector gene;
   a first chimeric protein comprising a nucleic acid binding protein that binds said peptide binding site where said nucleic acid binding protein is attached to said metabolic product or to a ligand that binds to said metabolic product; and
   a second chimeric protein comprising an expression control protein attached to said metabolic product or to said ligand that binds to said metabolic product such that when said first chimeric protein comprises said metabolic product, said second chimeric protein comprises said ligand and when said first chimeric protein comprises said ligand, said second chimeric protein comprises said metabolic product;
   wherein said expression control protein is a repressor.

5. The cell of claim 1, wherein said nucleic acid binding protein is selected from the group consisting of GAL-4, and GAL-4-Y.

6. The cell of claim 1, wherein said effector is selected from the group consisting of a reporter gene, a cytotoxin, and an apoptosis-inducing gene.

7. The cell of claim 1, wherein said reporter gene is selected from the group consisting of: chloramphenicol acetyl transferase (CAT), luciferase, b-galactosidase (b-gal), alkaline phosphatase, horse radish peroxidase (HRP), growth hormone (GH), and green fluorescent protein (GFP).

8. The cell of claim 1, wherein said effector encodes a cytotoxin selected from the group consisting of thymidine kinase, pseudomonas exotoxin, diphtheria toxin, ricin, and abrin.

9. The cell of claim 6, wherein said apoptosis-inducing gene is selected from the group consisting of P53, P73, Bax, Bad, FADD, and a caspase.

10. The cell of claim 1, wherein said ligand and said metabolic product respectively are selected from the group consisting of beta-catenin and a Tcf, a NF-kB and I-kB, a P53 and MDM2, a receptor and its heteromelic receptor partner.

11. The cell of claim 1, wherein said cell comprises a nucleic acid encoding said first chimeric protein.

12. The cell of claim 1, wherein said cell comprises a nucleic acid encoding said second chimeric protein.

13. The cell of claim 1, wherein
    said nucleic acid encodes a GAL-4 binding site, and said effector gene is a reporter gene;
    said first chimeric protein comprises a GAL-4 nucleic acid binding protein and a beta catenin or a Tcf; and,
    said second chimeric protein comprises a VP-16 and beta catenin or a Tcf.

14. The cell of claim 13, wherein said Tcf is Tcf4.

15. The cell of claim 1, wherein said cell further comprises a second nucleic acid encoding said ligand or metabolic product operably linked to an inducible promoter.

16. A nucleic acid comprising a nucleic acid selected from the group consisting of
    a nucleic acid encoding a chimeric protein comprising a nucleic acid binding domain attached to a Tcf4 or to a beta catenin, and
    a nucleic acid encoding a transactivator attached to a beta catenin or to a Tcf4.

17. The nucleic acid of claim 16, wherein said nucleic acid comprises a nucleic acid encoding a nucleic acid binding domain attached to a Tcf4.

18. The nucleic acid of claim 16, wherein said nucleic acid comprises a nucleic acid encoding a nucleic acid binding domain attached to a beta catenin.

19. The nucleic acid of claim 16, wherein said nucleic acid comprises a nucleic acid encoding a Tcf4 attached to a transactivator.

20. The nucleic acid of claim 16, wherein said nucleic acid comprises a nucleic acid encoding a beta catenin attached to a transactivator.

21. The nucleic acid of claim 16, wherein said nucleic acid is a DNA.

22. The nucleic acid of claim 16, wherein said nucleic acid is a vector.

23. A vector comprising:
a nucleic acid encoding a peptide binding site and an effector gene;
a nucleic acid encoding a first chimeric protein comprising a nucleic acid binding protein that binds said peptide binding site where said nucleic acid binding protein is attached to said metabolic product or to a ligand that binds to said metabolic product; and
a nucleic acid encoding a second chimeric protein comprising an expression control protein attached to said metabolic product or to said ligand that binds to said metabolic product such that when said first chimeric protein comprises said metabolic product, said second chimeric protein comprises said ligand and when said first chimeric protein comprises said ligand, said second chimeric protein comprises said metabolic product;
wherein said a nucleic acid encoding a first chimeric protein further encodes an HIV TAT domain attached to said first chimeric protein or;
wherein said a nucleic acid encoding a second chimeric protein further encodes an HIV TAT domain attached to said second chimeric protein.

24. A nucleic acid encoding a first chimeric protein comprising a nucleic acid binding protein attached to: a metabolic product or to a ligand that binds to a metabolic product;
wherein said nucleic acid further encodes an HIV TAT domain attached to said first chimeric protein.

25. A nucleic acid encoding a second chimeric protein comprising an expression control protein attached to a metabolic product or to a ligand that binds to said metabolic product;
wherein said nucleic acid further encodes an HIV TAT domain attached to said first chimeric protein.

26. A kit for screening for an agent that modulates the ability of a cell to accumulate or to degrade a metabolic product, said kit comprising:
a container containing a mammalian cell comprising:
a nucleic acid encoding a protein binding site and an effector gene;
a first chimeric protein comprising a nucleic acid binding protein that binds said protein binding site attached to said metabolic product or to a ligand that binds to said metabolic product;
a second chimeric protein comprising an expression control protein attached to said metabolic product or to said ligand that binds to said metabolic product such that when said first chimeric protein comprises said metabolic product, said second chimeric protein comprises said ligand and when said first chimeric protein comprises said ligand, said second chimeric protein comprises said metabolic product.

27. A kit for screening for an agent that modulates the ability of a cell to accumulate or to degrade a metabolic product, said kit comprising: a container containing a nucleic acid of claim 16.

28. A kit for selectively killing a cell, said kit comprising a container containing a two-hybrid system component selected from the group consisting of:
a nucleic acid of claim 16, and
a protein encoded by a nucleic acid of claim 16.

* * * * *